US008585615B2

(12) United States Patent
Kasahara et al.

(10) Patent No.: US 8,585,615 B2
(45) Date of Patent: Nov. 19, 2013

(54) ABDOMINAL OBESITY INDEX MEASURING APPARATUS

(75) Inventors: Yasuhiro Kasahara, Asaka (JP); Yoshio Sakai, Shiki (JP); Hirokazu Ono, Kawasaki (JP); Koji Tsuji, Niiza (JP)

(73) Assignee: Tanita Corporation, Itabashi-Ku, Tokyo (JP)

( * ) Notice: Subject to any disclaimer, the term of this patent is extended or adjusted under 35 U.S.C. 154(b) by 200 days.

(21) Appl. No.: 13/167,386

(22) Filed: Jun. 23, 2011

(65) Prior Publication Data

US 2012/0016268 A1 Jan. 19, 2012

(30) Foreign Application Priority Data

Jul. 14, 2010 (JP) ................................ 2010-159522

(51) Int. Cl.
*A61B 5/05* (2006.01)
*A61B 5/103* (2006.01)
*A61B 5/117* (2006.01)

(52) U.S. Cl.
USPC ........................... 600/587; 600/547; 600/593

(58) Field of Classification Search
USPC ........................................ 600/587, 593, 547
See application file for complete search history.

(56) References Cited

U.S. PATENT DOCUMENTS

| | | | | |
|---|---|---|---|---|
| 6,643,542 B1* | 11/2003 | Kawanishi | ...................... | 600/547 |
| 6,752,760 B2* | 6/2004 | Kouou | ............................ | 600/301 |
| 6,905,464 B2* | 6/2005 | Kawanishi et al. | ............ | 600/301 |
| 6,978,170 B1* | 12/2005 | Onda et al. | ..................... | 600/547 |
| 7,283,869 B2* | 10/2007 | Onda et al. | ..................... | 600/547 |
| 7,594,896 B2* | 9/2009 | Sakai et al. | ..................... | 600/587 |
| 7,813,795 B2* | 10/2010 | Sakai | ............................. | 600/547 |
| 7,925,340 B2* | 4/2011 | Masuo et al. | .................. | 600/547 |
| 7,957,795 B2* | 6/2011 | Tsuji | .............................. | 600/547 |
| 7,962,205 B2* | 6/2011 | Okura et al. | ................... | 600/547 |
| 8,295,570 B2* | 10/2012 | Markwardt et al. | ........... | 382/128 |
| 2002/0151815 A1* | 10/2002 | Kawanishi et al. | ............ | 600/547 |
| 2004/0077969 A1* | 4/2004 | Onda et al. | ..................... | 600/547 |

(Continued)

FOREIGN PATENT DOCUMENTS

| | | |
|---|---|---|
| CN | 1679442 A | 10/2005 |
| CN | 101112310 A | 1/2008 |

(Continued)

OTHER PUBLICATIONS

European Search Report issued by the European Patent Office on Nov. 11, 2011 in European Application No. 11711719.

(Continued)

*Primary Examiner* — Jeffrey G Hoekstra
*Assistant Examiner* — May Abouelela
(74) *Attorney, Agent, or Firm* — Buchanan Ingersoll & Rooney PC

(57) ABSTRACT

An abdomen width determiner determines an abdomen width of a subject. A shape index calculator calculates a shape index corresponding to a cross-sectional shape of an abdomen of the subject. An obesity evaluator evaluates whether an obesity degree of the subject is high or low. An obesity index calculator calculates an obesity index corresponding to the abdomen width using a first equation if the obesity evaluator evaluates that the obesity degree is low, and calculates an obesity index corresponding to the abdomen width and the shape index using a second equation different from the first equation if the obesity evaluator evaluates that the obesity degree is high.

9 Claims, 16 Drawing Sheets

(56) References Cited

U.S. PATENT DOCUMENTS

| | | | |
|---|---|---|---|
| 2005/0107717 A1* | 5/2005 | Yamamoto et al. | 600/547 |
| 2005/0222516 A1* | 10/2005 | Kasahara et al. | 600/547 |
| 2006/0025701 A1* | 2/2006 | Kasahara | 600/547 |
| 2008/0021349 A1* | 1/2008 | Sakai et al. | 600/587 |
| 2008/0221476 A1* | 9/2008 | Sakai | 600/547 |
| 2008/0319338 A1* | 12/2008 | Kawanishi | 600/547 |
| 2009/0024053 A1 | 1/2009 | Kasahara | |
| 2011/0112430 A1 | 5/2011 | Karo et al. | |
| 2011/0152723 A1 | 6/2011 | Kasahara | |

FOREIGN PATENT DOCUMENTS

| | | |
|---|---|---|
| EP | 1 882 447 A1 | 1/2008 |
| EP | 1 882 448 A1 | 1/2008 |
| EP | 2 016 895 A1 | 1/2009 |
| EP | 2 335 577 A1 | 6/2011 |
| JP | 2001-212111 A | 8/2001 |
| JP | 2003-93363 A | 4/2003 |
| JP | 2007-111166 A | 5/2007 |
| JP | 2008-049114 A | 3/2008 |
| JP | 2009-022482 A | 2/2009 |
| WO | WO 2010/032836 A1 | 3/2010 |

OTHER PUBLICATIONS

Chinese Office Action issued Jan. 16, 2013 by the State Intellectual Property Office of P.R. China in Chinese Patent Application No. 201110199944.2 and English language translation.

* cited by examiner

|  | MALE (NUMBER OF SAMPLES: 112) | FEMALE (NUMBER OF SAMPLES: 77) |
|---|---|---|
| AGE | 49.1 ± 13.6 | 50.6 ± 14.2 |
|  | 19 to 72 | 21 to 71 |
| BMI | 27.1 ± 4.5 | 28.7 ± 5.3 |
|  | 16.1 to 40.3 | 18.6 to 48.6 |
| ABDOMINAL CIRCUMFERENCE | 93.2 ± 12.3 | 95.8 ± 12.3 |
|  | 63.0 to 124.6 | 66.0 to 121.4 |

UPPER: AVERAGE ± STANDARD DEVIATION
LOWER: RANGE (MIN to MAX)

|  | AGE | BMI | ABDOMINAL CIRCUMFERENCE |
|---|---|---|---|
| MALE, FEMALE (NUMBER OF SAMPLES: 210) | 49.5 ± 13.8 | 27.2 ± 5.1 | 93.1 ± 12.7 |
|  | 19 to 72 | 16.1 to 48.6 | 62.8 to 128.4 |

UPPER: AVERAGE ± STANDARD DEVIATION
LOWER: RANGE (MIN to MAX)

ABDOMINAL OBESITY INDEX MEASURING APPARATUS

BACKGROUND OF THE INVENTION

1. Field of the Invention

The present invention relates to a technology for estimating an index relating to obesity (hereinafter, referred to as an "obesity index").

2. Related Art

Technologies for calculating an obesity index from an abdomen width of a subject have been conventionally proposed. For example, Patent Document 1 discloses a technology for calculating an obesity index such as a visceral fat area using an equation including an abdomen width of a subject as a variable. Furthermore, Patent Document 2 discloses a technology for calculating an abdominal circumference of a subject using an equation including an abdomen width as a variable.

Patent Document 1: JP-A-2009-022482
Patent Document 2: JP-A-2008-049114

According to the technologies of Patent Documents 1 and 2, the obesity index can be determined with high accuracy for a subject with a standard body type. However, a tendency for the accuracy in determining the obesity index to decrease as the degree of obesity of a subject increases has been confirmed in a study by the present inventors. In view of the above circumstances, the present invention aims to also be able to determine an obesity index with high accuracy for a subject who is very obese.

SUMMARY OF THE INVENTION

Means employed by the present invention to solve the above problem are described. To facilitate understanding of the present invention, correspondences between respective elements of the present invention and elements of respective embodiments described later are written in parentheses, but this is not intended to limit the scope of the present invention to the constructions of the embodiments.

In accordance with an aspect of the present invention, a measuring apparatus includes: an abdomen width determining unit (e.g., abdomen width determiner 642) for determining an abdomen width (e.g., abdomen width AW) of a subject; an obesity evaluating unit (e.g., obesity evaluator 662) for evaluating whether an obesity degree of the subject is high or low; and an obesity index calculating unit (e.g., obesity index calculator 664) for calculating an obesity index corresponding to the abdomen width using a first equation (e.g., equation (1) or equation (3)) when the obesity evaluating unit evaluates that the obesity degree is low and calculating an obesity index corresponding to the abdomen width using a second equation (e.g., equation (2) or equation (4)) different from the first equation when the obesity evaluating unit evaluates that the obesity degree is high. As a result, the first and second equations are selectively used depending on the obesity degree of the subject for calculation of the obesity index corresponding to the abdomen width. Therefore, an obesity index of an obese person can be calculated with high accuracy.

A measuring apparatus according to a preferred aspect of the present invention includes a shape index calculating unit (e.g., shape index calculator 644) for calculating a shape index corresponding to a cross-sectional shape of an abdomen of the subject, and the second equation includes the shape index as a variable. In the above aspect, the second equation used for a subject with a high obesity degree includes a shape index corresponding to a cross-sectional shape. Since the cross-sectional shape of the abdomen differs depending on the obesity type (visceral fat type versus subcutaneous fat type) of the subject, there is an advantage in being able to calculate the obesity index with high accuracy regardless of whether the obesity type is the visceral fat type or the subcutaneous fat type, according to the above aspect.

A measuring apparatus according to a preferred aspect of the present invention includes a measuring portion (e.g., measuring portion 40) for generating a distance measurement signal corresponding to a distance to a measurement point on a measurement line on an abdomen surface of the subject for each of a plurality of measurement lines (e.g., measurement lines M[1] to M[N]) which are parallel to a lateral direction of the subject and located at different positions in forward and backward directions, and the shape index calculating unit calculates the shape index corresponding to a discrepancy between a first distance (LA[n], LB[n]) indicated by a distance measurement signal corresponding to a determination line (e.g., determination line MW) with a longest section passing through the abdomen out of the plurality of the measurement lines and a second distance (LA[N], LB[N]) indicated by a distance measurement signal corresponding to a reference line (e.g., reference line MREF) selected from the plurality of the measurement lines. The position in forward and backward directions of the subject where the lateral width of the abdomen is greatest (maximum abdomen width) differs depending on the fat type of the subject. Thus, according to the above aspect in which the shape index is calculated based on the discrepancy between the first distance corresponding to the determination line close to the position of the maximum abdomen width and the second distance corresponding to the reference line selected from the plurality of measurement lines, a change in the cross-sectional shape of the abdomen resulting from the fat type of the subject can be appropriately reflected in the shape index.

In a preferred aspect of the present invention, the measuring portion includes a first distance meter (e.g., distance meter 42A) and a second distance meter (e.g., distance meter 42B) which face each other across the abdomen of the subject and each of which generates the distance measurement signals corresponding to the respective measurement lines; and the shape index calculating unit calculates the shape index corresponding to a discrepancy between a sum (e.g., total distance TW) of first distances (LA[n], LB[n]) indicated by the distance measurement signals generated for the determination line by the respective first and second distance meters and a sum (e.g., total distance TREF) of second distances (LA[N], LB[N]) indicated by the distance measurement signals generated for the reference line by the respective first and second distance meters. In the above aspect, the sums of the distances indicated by the distance measurement signals generated by the respective first and second distance meters facing each other across the abdomen of the subject are used to calculate the shape index. Thus, there is an advantage of being able to calculate an appropriate shape index corresponding to the cross-sectional shape of the abdomen, for example, even if the cross-sectional shape of the abdomen of the subject is asymmetric or the abdomen of the subject deviates from a predetermined position (e.g., position equidistant from the first and second distance meters).

In a preferred aspect of the present invention, the abdomen width determining unit determines a numerical value obtained by subtracting the first distances indicated by the distance measurement signals generated for the determination line by the respective first and second distance meters from a distance (e.g., distance L0) between the first and second distance meters as the abdomen width. In the above aspect, since the first and second distances used to calculate the shape index are also used to determine the abdomen width by the abdomen width determining unit, there is an advantage of reducing a computation amount as compared with a construction in which the shape index and the abdomen width are independently calculated.

In a preferred aspect of the present invention, the obesity index is a visceral fat area of the subject, and the shape index calculating unit calculates the shape index so that the more distant from the back surface (e.g., reference plane PREF) of the subject in the forward and backward directions of the subject at a position where the abdomen width is greatest, the greater the visceral fat area calculated by the obesity index calculating unit. In the above aspect, the shape index is so calculated that the more distant from the back surface of the subject the position of the maximum abdomen width (visceral fat type), the greater the visceral fat area. As a result, it is possible to calculate a visceral fat area appropriately reflecting a difference in the cross-sectional shape of the abdomen resulting from the fat type.

In a further preferred aspect of the present invention, the obesity index calculating unit calculates a visceral fat area corresponding to the abdomen width using the first equation (e.g., equation (1)), evaluates the visceral fat area to be the calculated value if the obesity evaluating unit evaluates that the obesity degree is low, and calculates a visceral fat area using the second equation (e.g., equation (2)) including the visceral fat area calculated by the first equation as the variable if the obesity evaluating unit evaluates that the obesity degree is high. In the above aspect, since the visceral fat area calculated by the first equation is used for the second equation, there is an advantage of reducing a computation amount as compared with a construction in which the calculation by the second equation is performed independently of that by the first equation.

In a preferred aspect of the present invention, the obesity index is an abdominal circumference of the subject, and the shape index calculating unit calculates the shape index so that the more distant from the back surface of the subject in the forward and backward directions of the subject at a position where the abdomen width is greatest, the greater the numerical value of the abdominal circumference calculated by the obesity index calculating unit. In the above aspect, the shape index is so calculated that the more distant from the back surface of the subject the position of the maximum abdomen width (visceral fat type), the greater the abdominal circumference. As a result, it is possible to calculate an abdominal circumference appropriately reflecting a difference in the cross-sectional shape of the abdomen resulting from the fat type.

In a preferred aspect of the present invention, the obesity evaluating unit evaluates whether the obesity degree of the subject is high or low based on the abdomen width determined by the abdomen width determining unit. In the above aspect, since the abdomen width used to calculate the obesity index is used to evaluate the obesity index, there is an advantage of reducing a computation amount as compared with a construction in which an index without relationship to the calculation of the obesity index by the obesity index calculating unit is used to evaluate the obesity index.

The measuring apparatus according to each of the above aspects is realized, for example, by cooperation of an arithmetic processing apparatus and a program (software). A program of the present invention causes a computer to perform an abdomen width determining process for determining an abdomen width of a subject, an obesity evaluating process for evaluating whether an obesity degree of the subject is high or low, and an obesity index calculating process for calculating an obesity index corresponding to the abdomen width using a first equation when the obesity evaluating unit evaluates that the obesity degree is low and calculating an obesity index corresponding to the abdomen width using a second equation different from the first equation when the obesity evaluating unit evaluates that the obesity degree is high. According to the above program, functions and effects similar to those of the measuring apparatus of the present invention are realized. In addition to being installed in a computer by being provided to a user in a form stored in a computer-readable storage medium, the program of the present invention may be installed in a computer by being provided from a server by delivery via a communication network.

DETAILED DESCRIPTION OF PREFERRED EMBODIMENTS

First Embodiment

Figure 1:
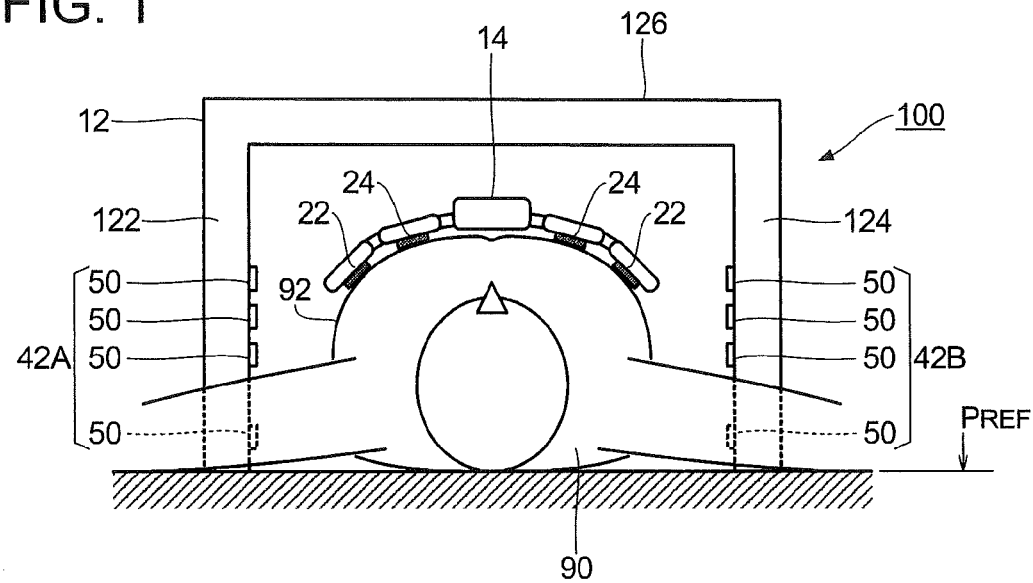
FIG. 1 is a front view of a measuring apparatus according to a first embodiment of the present invention.

FIG. 1 is a front view of a measuring apparatus 100 according to a first embodiment. The measuring apparatus 100 is a piece of measuring equipment for measuring (estimating) an obesity index of a subject 90 lying on his back with his back surface held in contact with a reference plane (e.g., a surface of a bed or the like) $P_{REF}$. In the first embodiment, a visceral fat area is measured as an obesity index. As shown in FIG. 1, the measuring apparatus 100 includes a main unit 12 and an electrode unit 14. The main unit 12 and the electrode unit 14 communicate with each other in a wired or wireless manner.

Figure 2:
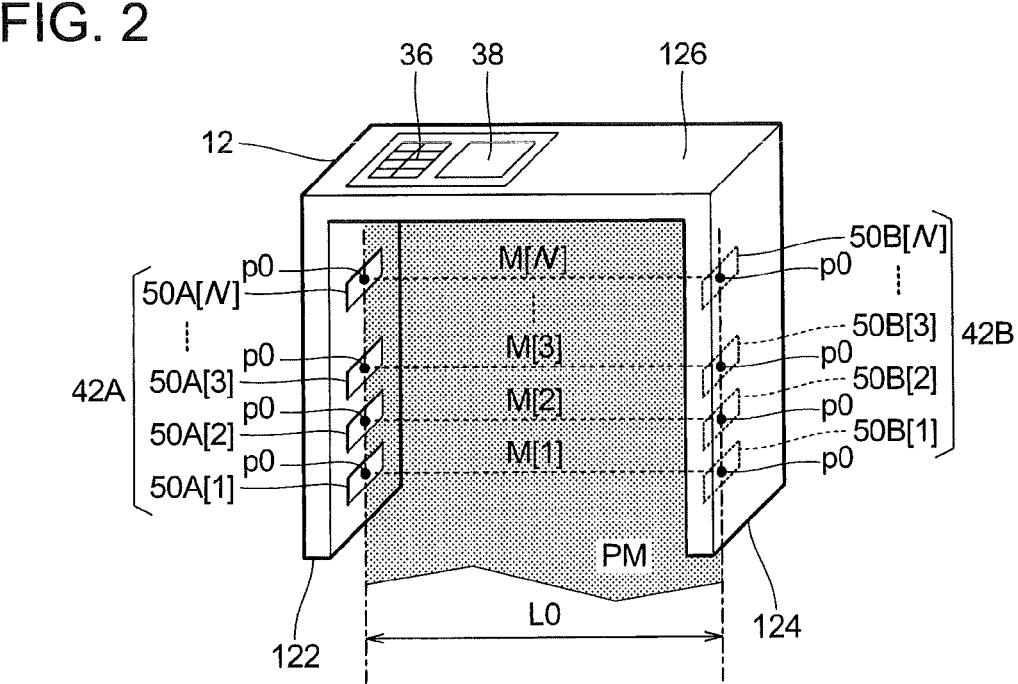
FIG. 2 is a perspective view of a main unit.

FIG. 2 is a front view of the main unit 12. As shown in FIGS. 1 and 2, the main unit 12 includes legs 122 and 124 extending substantially in parallel while being spaced apart from each other and a long supporting portion 126 connecting each end of the legs 122 and 124. Specifically, the main unit 12 of the first embodiment is a substantially rectangular frame with an open lower side. As shown in FIG. 1, the main unit 12 is so arranged on the reference plane $P_{REF}$ that the respective bottom surfaces of the legs 122 and 124 are in contact with the reference plane $P_{REF}$ with an abdomen 92 of a subject 90 surrounded by the legs 122 and 124 and the supporting portion 126 as shown in FIG. 1. The electrode unit 14 is used for measurement of biological impedance by being placed on the abdomen 92 of the subject 90.

Figure 3:
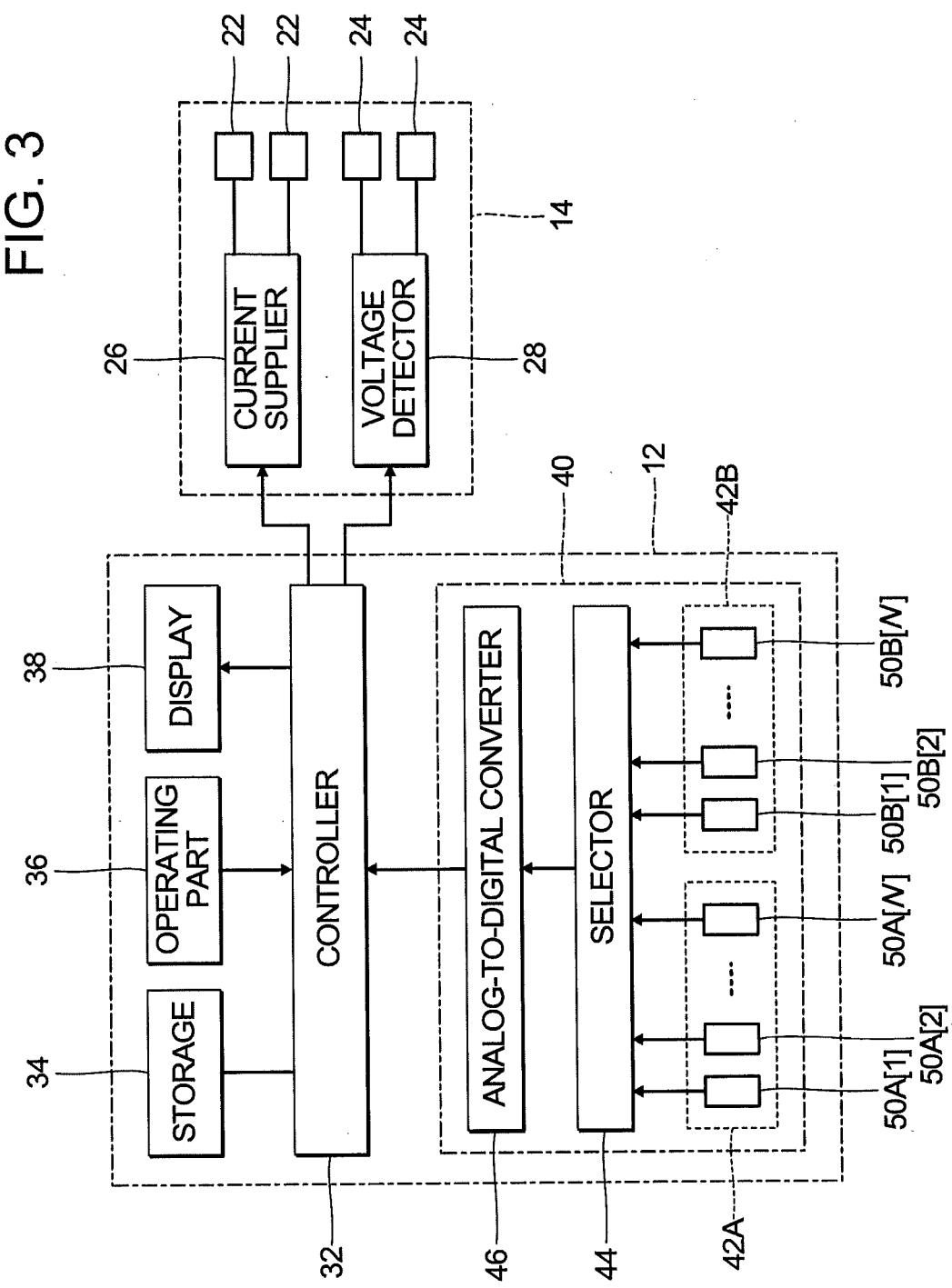
FIG. 3 is a block diagram of the electrical construction of the measuring apparatus.

FIG. 3 is a block diagram showing the electrical construction of the measuring apparatus 100. As shown in FIG. 3, the electrode unit 14 includes a pair of current supplying electrodes 22, a pair of voltage measuring electrodes 24, a current supplier 26 and a voltage detector 28. As shown in FIG. 1, the respective current supplying electrodes 22 are separated from each other and held in contact with the abdomen 92 of the subject 90. The respective voltage measuring electrodes 24 are separated from each other at the inner sides of the respective current supplying electrodes 22 and held in contact with the abdomen 92 of the subject 90.

The current supplier 26 of FIG. 3 supplies a measurement current between the respective current supplying electrodes 22. The measurement current is an alternating current with a frequency FH or FL (FH>FL) which is routed through the interior of the abdomen 92 of the subject 90. The frequency FH may be set at 50 kHz, and the frequency FL may be set at 6.25 kHz. The voltage detector 28 detects a voltage between the respective voltage measuring electrodes 24 (hereinafter, referred to as a "detection voltage") in a period during which the measurement current is supplied to the abdomen 92 of the subject 90. The detection voltage is transmitted to the main unit 12 (controller 32) after being converted into a digital signal by an A/D converter (not shown).

As shown in FIG. 3, the controller 32, a storage 34, an operating part 36, a display 38 and a measuring portion 40 are installed in the main unit 12. The controller 32 (CPU) controls the respective elements of the measuring apparatus 100 by implementing a program stored in the storage 34. The storage 34 is a storage circuit which stores the program implemented by the controller 32 and various data used by the controller 32 and includes, for example, a ROM and a RAM.

The operating part 36 includes, for example, a plurality of manipulandums and receives instructions from a user. For example, the sex (male or female) of the subject 90 is designated through an operation on the operating part 36. The display 38 (e.g., liquid crystal display device) displays various images under the control of the controller 32. For example, the display 38 displays guidance of a measurement procedure using the measuring apparatus 100 and an obesity index estimated for the subject 90. As shown in FIG. 2, the operating part 36 and the display 38 are arranged on a surface of the main unit 12.

The measuring portion 40 of FIG. 3 includes distance meters 42A and 42B, a selector 44 and an A/D (analog-to-digital) converter 46 and generates electrical signals corresponding to the size of the abdomen 92 of the subject 90 (hereinafter, referred to as "distance measurement signals"). As shown in FIG. 2, the distance meter 42A is made up of N distance measuring sensors 50 (50A[1] to 50A[N]) arranged at intervals from each other on a surface of the leg 122 facing the leg 124. Similarly, the distance meter 42B is made up of N distance measuring sensors 50 (50B[1] to 50B[N]) arranged at intervals from each other on a surface of the leg 124 facing the leg 122. The distance measuring sensor 50A[n] (n=1 to N) is the $n^{th}$ distance measuring sensor of the distance meter 42A counted from the bottom surface of the leg 122 (from a side opposite to the supporting portion 126). Similarly, the distance measuring sensor 50B[n] is the $n^{th}$ distance measuring sensor from the bottom surface of the leg 124.

Figure 4:
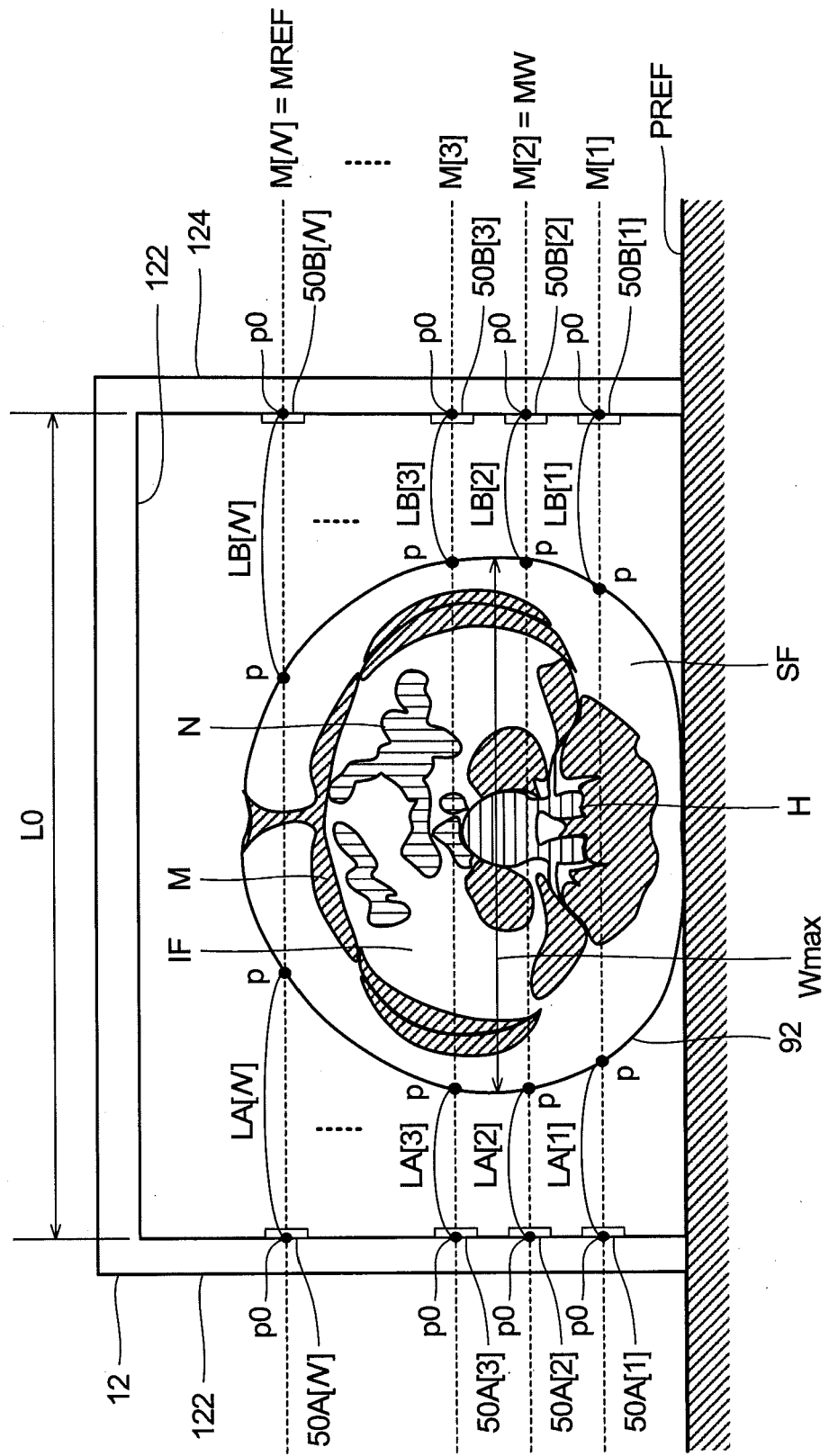
FIG. 4 is a diagram showing the abdomen of a subject and the main unit.

FIG. 4 is a diagram showing a relationship between a transverse section of the abdomen 92 of the subject 90 lying on his back on the reference plane $P_{REF}$ and the respective distance measuring sensors 50 (50A[1] to 50A[N], 50B[1] to 50B [N]) of the main unit 12. As shown in FIGS. 1 and 4, the respective distance measuring sensors 50 are noncontact (optical) distance measuring elements facing the abdomen 92 of the subject 90. Specifically, the distance measuring sensors 50 generate distance measurement signals corresponding to distances L (LA[1] to LA[N], LB[1] to LB [N]) between reference points p0 therein and measurement points p to be measured on the surface of the abdomen 92 of the subject 90. The measurement points p are equivalent to intersections of distance measurement axes passing through the reference points p0 and the surface of the abdomen 92 facing the distance measuring sensors 50. Each distance measuring sensor 50 includes, for example, a light emitting element for emitting a ray of light such as infrared light in a direction of the distance measurement axis, and a light receiving element for generating a distance measurement signal corresponding to the amount of received light reflected at the measurement point out of the light emitted from the light emitting element.

As shown in FIG. 2, N distance measuring sensors 50A[1] to 50A[N] and N distance measuring sensors 50B[1] to 50B [N] are arranged such that the reference points p0 of the respective distance measuring sensors 50 are located in a common plane (hereinafter, referred to as a "measurement plane") PM. The measurement plane PM is a plane crossing the abdomen 92 of the subject 90 (plane perpendicular to the reference plane $P_{REF}$) with the main unit 12 placed on the reference plane $P_{REF}$. Ideally, the main unit 12 is placed on the reference plane $P_{REF}$ so that the measurement plane PM passes the navel of the subject 90.

As shown in FIG. 4, the $n^{th}$ distance measuring sensor 50A[n] of the distance meter 42A and the $n^{th}$ distance measuring sensor 50B[n] of the distance meter 42B are arranged at positions facing each other across the abdomen 92 of the subject 90. Specifically, assuming N measurement lines M[1] to M[N], which are parallel to the lateral direction of the subject 90 and located at different positions in forward and backward directions (at different distances from the reference plane $P_{REF}$), in the measurement plane PM, the distance measurement axes (reference points p0) of both distance measuring sensors 50A[n], 50B[n] are located on a common measurement line M[n]. In other words, the reference point p0 of the distance measuring sensor 50A[n] and that of the distance measuring sensor 50B[n] are at positions equidistant from the reference plane $P_{REF}$. A distance L0 between the reference points p0 of the distance measuring sensors 50A[n] and 50B[n] facing each other is common among N pairs.

As shown in FIG. 4, concerning various possible body types of the subject 90, a distribution range of the respective distance measuring sensors 50 are so statistically or empirically selected that a maximum lateral value (hereinafter, referred to as a "maximum abdomen width") $W_{max}$ of the abdomen 92 in the measurement plane PM is located between the measurement line M[1] closest to the reference plane $P_{REF}$ and the measurement line M[N] most distant from the reference plane $P_{REF}$. For example, if N is four, a distance between the reference plane $P_{REF}$ and the closest distance measuring sensor 50A[1] is set at about 4 cm and intervals between adjacent ones of the respective distance measuring sensors 50A[n] are set at about 3 cm.

In the above construction, each distance measuring sensor 50A[n] of the distance meter 42A generates and outputs a distance measurement signal corresponding to a distance LA[n] between the measurement point p where the surface of the abdomen 92 of the subject 90 facing this distance measuring sensor 50A[n] and the measurement line M[n] intersect and the reference point p0 of the distance measuring sensor 50A[n]. Similarly, each distance measuring sensor 50B[n] of the distance meter 42B generates and outputs a distance measurement signal corresponding to a distance LB[n] between the measurement point p where the measurement line M[n] intersects with the abdomen 92 and the reference point p0 of the distance measuring sensor 50B[n]. The selector 44 of FIG. 3 successively selects the distance measurement signals generated in parallel by the respective distance measuring sensors 50 in a time division manner and supplies them to the A/D converter 46. The A/D converter 46 converts the distance measurement signals supplied from the selector 44 into digital signals and supplies them to the controller 32. Note that, since the abdomen 92 is deformed when the electrode unit 14 is placed thereon, measurement of the size of the abdomen 92 utilizing the measuring portion 40 (generation of the distance measurement signals) is performed without the electrode unit 14 placed on the abdomen 92.

Figure 5:
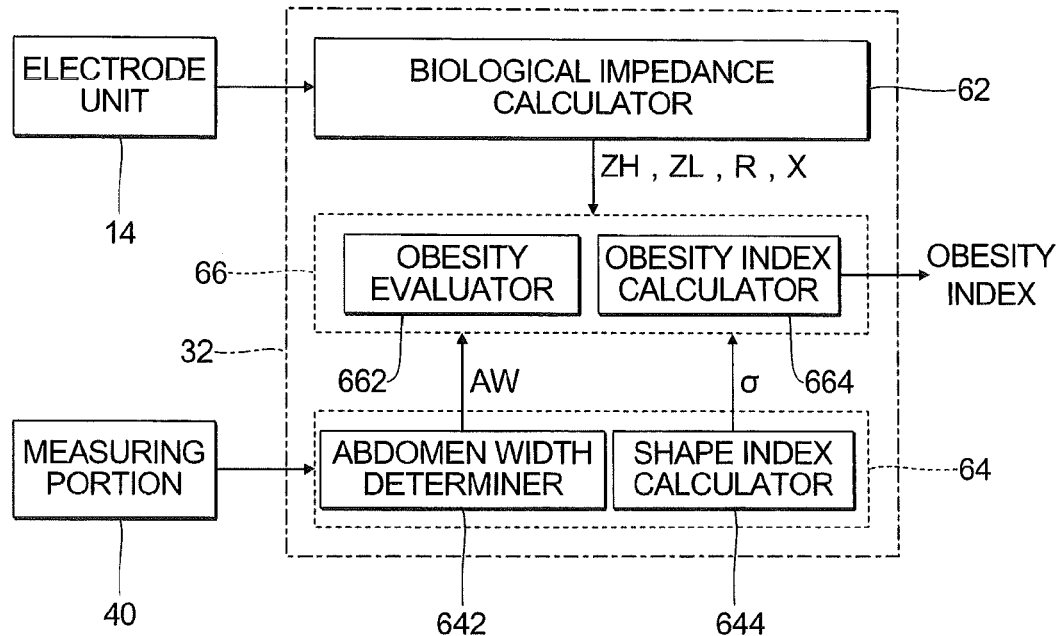
FIG. 5 is a block diagram showing the functional construction of a controller.

FIG. 5 is a diagram showing the function of the controller 32. The controller 32 functions as elements (biological impedance calculator 62, a distance measurement value processor 64, an arithmetic processor 66) of FIG. 5 to calculate a visceral fat area (obesity index) of the subject 90 by implementing the program stored in the storage 34. Note that a construction in which the respective functions of the controller 32 are scattered over a plurality of integrated circuits and a construction in which the respective functions are realized by a special electronic circuit (DSP) may also be employed.

The biological impedance calculator 62 successively calculates biological impedances (ZH, ZL) of the subject 90 and stores them in the storage 34. Specifically, the biological impedance calculator 62 calculates the biological impedance ZH based on a relationship between the detection voltage and the measurement current in a period of supplying the measurement current having the frequency FH between the current supplying electrodes 22, and calculates the biological impedance ZL based on a relationship between the detection voltage and the measurement current in a period of supplying the measurement current having the frequency FL between the current supplying electrodes 22. The biological impedance calculator 62 also calculates a resistance component value (resistance) R and a capacitance component value (reactance) X of the abdomen 92 of the subject 90 based on a phase difference between the biological impedance ZH having the frequency FH and the measurement current. Any known technology may be employed for calculation by the biological impedance calculator 62.

The distance measurement value processor 64 of FIG. 5 calculates a variable used for calculation of the visceral fat area by processing the distance measurement signals generated by the measuring portion 40. As shown in FIG. 5, the distance measurement value processor 64 includes an abdomen width determiner 642 and a shape index calculator 644. The abdomen width determiner 642 determines an abdomen width AW of the subject 90. The abdomen width AW means an estimated value of the maximum abdomen width $W_{max}$ of the subject 90 (i.e., maximum value of the lateral width in the transverse section of the abdomen 92). The shape index calculator 644 calculates a shape index a corresponding to the cross-sectional shape of the abdomen 92 in the measurement plane PM.

Figure 6:
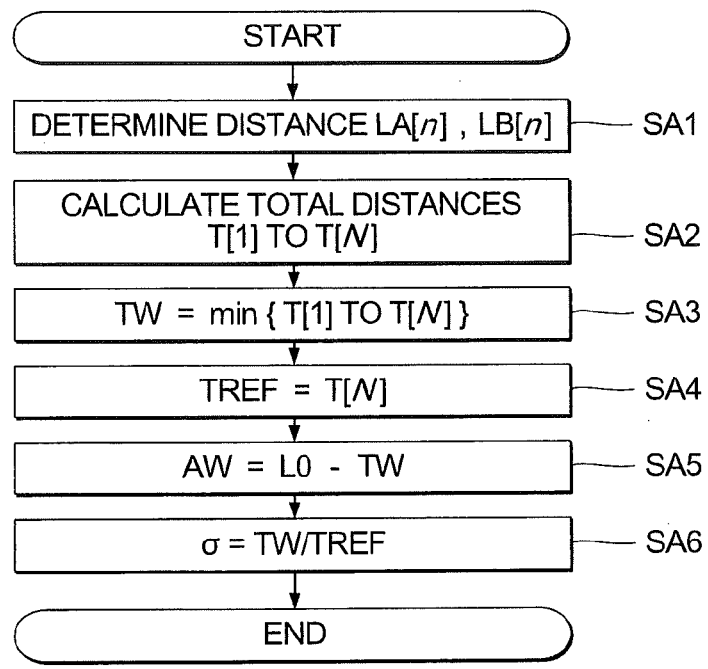
FIG. 6 is a flow chart showing the operation of a distance measurement value processor.

FIG. 6 is a flow chart showing the operation of the distance measurement value processor 64. A process of FIG. 6 is started upon the supply of the distance measurement signals from the measuring portion 40. The distance measurement value processor 64 determines the distances LA[1] to LA[N] and the distances LB[1] to LB[N] based on the distance measurement signals generated by the measuring portion 40 (SA1) and calculates a total distance T[n] of the distances LA[n] and LB[n] corresponding to the measurement line M[n] for each of the N measurement line M[1] to M[N] (SA2). The total distance T[n] (T[n]=LA[n]+LB[n]) is equivalent to a total value of the distances (LA[n], LB[n]) from the distance measuring sensors 50A[n], 50B[n] facing each other to the surface of the abdomen 92 of the subject 90.

The distance measurement value processor 64 selects a minimum value (min) of N total distance T[1] to T[N] as a distance TW (SA3). Since the distance L0 between the distance measuring sensors 50A[n] and 50B[n] is common among N pairs, the distance TW is the total distance T[n] on the measurement line M[n] overlapping with the abdomen 92 of the subject 90 most (hereinafter, referred to as a "determination line MW") out of N measurement lines M[1] to M[N]. Accordingly, the determination line MW is closest to the position of the maximum abdomen width $W_{max}$ in forward and backward directions of the subject 90 among N measurement lines M[1] to M[N]. FIG. 4 illustrates a case in which the measurement line M[2] is selected as the determination line MW. Furthermore, the distance measurement value processor 64 selects the total distance T[N] corresponding to the measurement line M[N] (may be particularly referred to as a "reference line $M_{REF}$" below) most distant from the reference plane $P_{REF}$ out of N measurement lines M[1] to M[N] as a distance $T_{REF}$ (SA4).

The abdomen width determiner 642 calculates the abdomen width AW by subtracting the distance TW calculated in step SA3 from the distance L0 between the respective distance measuring sensors 50A[n] and the respective distance measuring sensors 50B[n] (AW=L0−TW) (SA5). Since the determination line MW is closest to the position of the maximum abdomen width $W_{max}$, the abdomen width AW (unit: cm$^2$) obtained by subtracting the distance TW corresponding to the determination line MW from the distance L0 is equivalent to a numerical value approximate to or matching the maximum abdomen width $W_{max}$ (i.e., an estimated value of the maximum abdomen width $W_{max}$).

The shape index calculator 644 calculates the shape index σ from the distance TW calculated in step SA3 and the distance $T_{REF}$ calculated in step SA4 (SA6). Specifically, the shape index calculator 644 calculates a numerical value of a ratio of the distance TW to the distance $T_{REF}$ as the shape index σ (σ=TW/$T_{REF}$). The distance measurement value processor 64 operates as described above.

Figure 7:
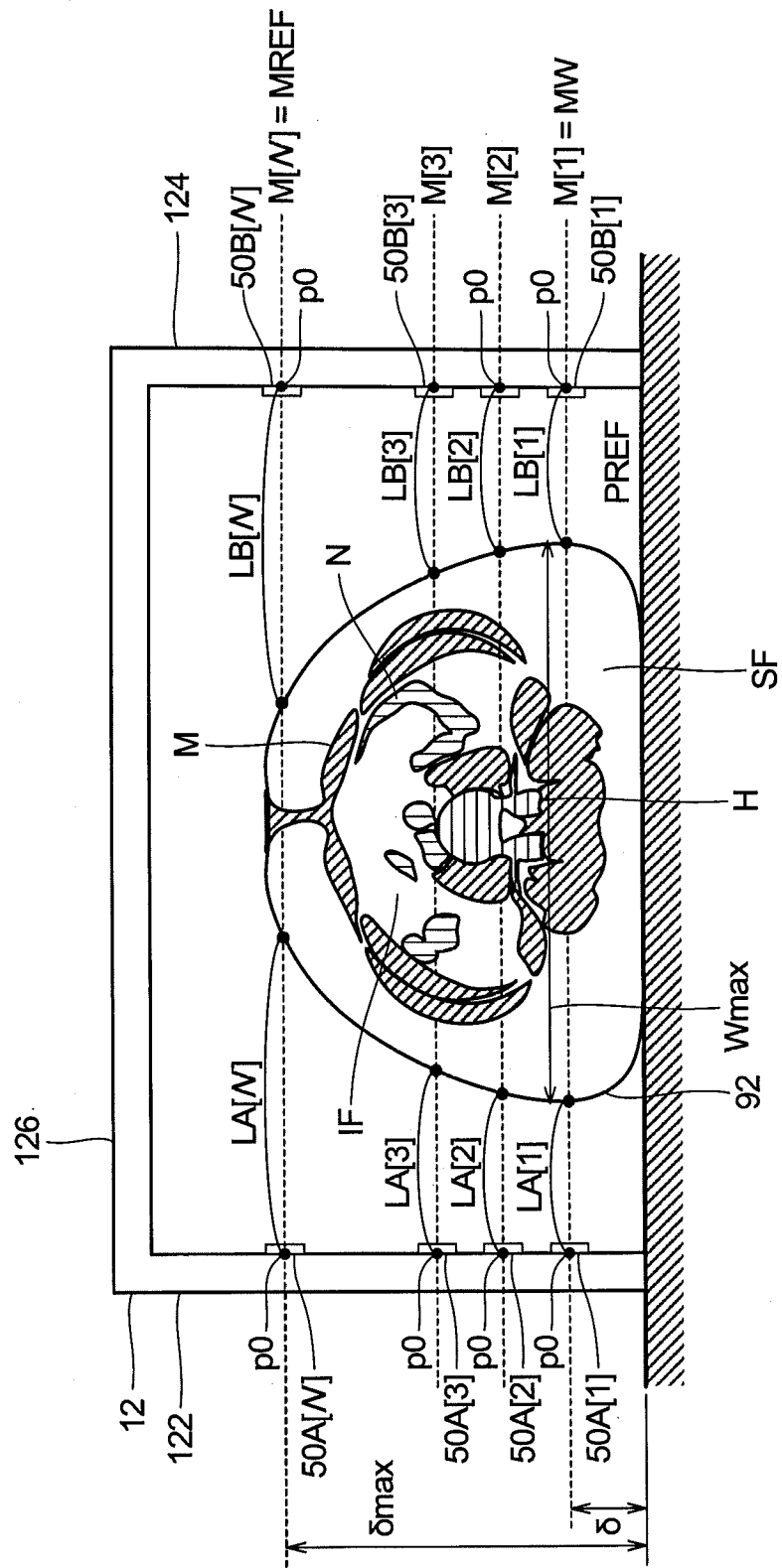
FIG. 7 is a diagram showing a cross-sectional shape of a subcutaneous fat type abdomen.
Figure 8:
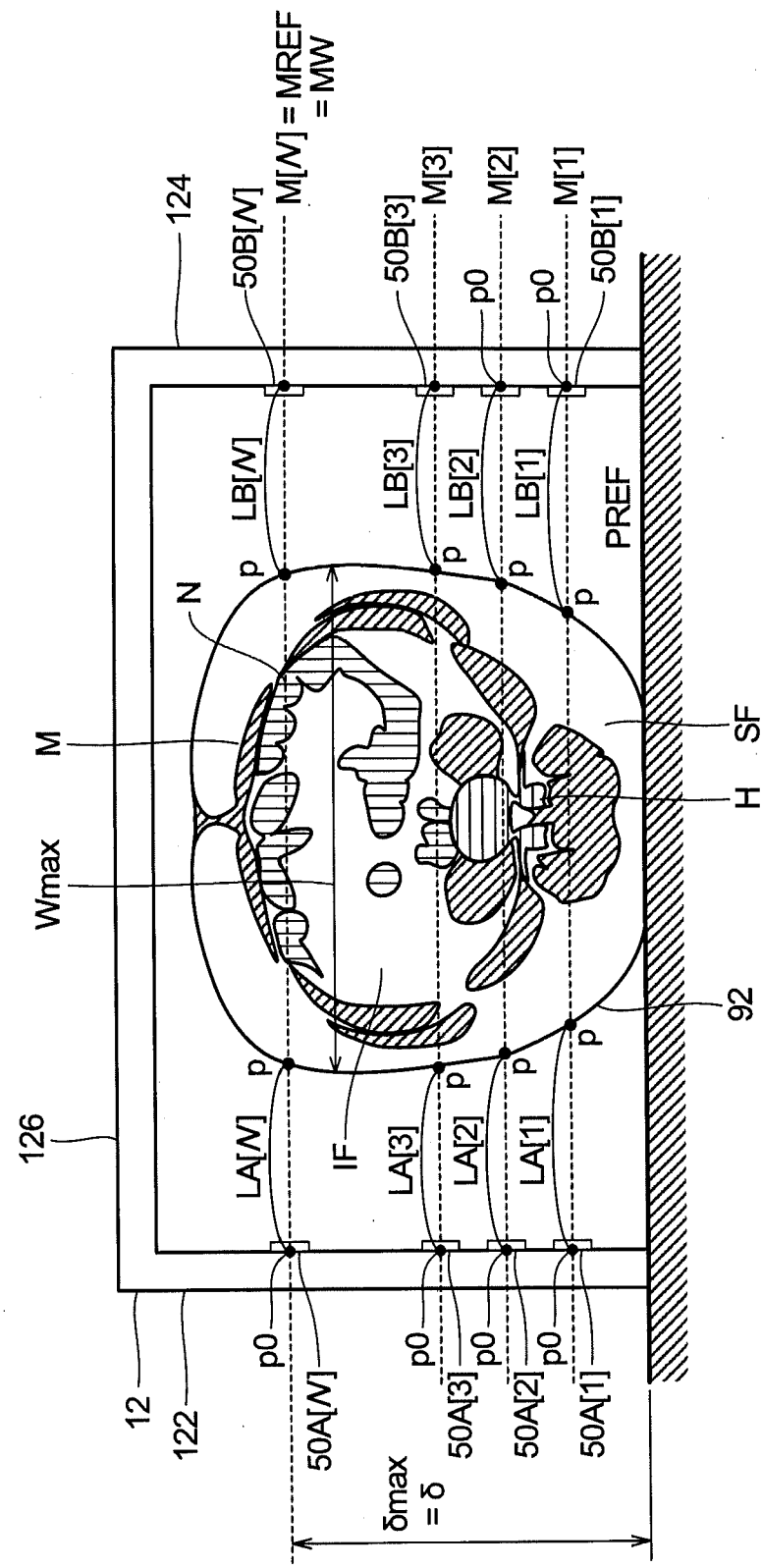
FIG. 8 is a diagram showing a cross-sectional shape of a visceral fat type abdomen.

Next, the meaning of the shape index σ will be described. FIG. 7 shows a transverse section of a subcutaneous fat type abdomen 92 and FIG. 8 shows a transverse section of a visceral fat type abdomen 92. In FIGS. 7 and 8, respective parts (bone H, inner organ N, muscle M, subcutaneous fat SF, visceral fat IF) in the transverse section of the abdomen 92 are shown. The subcutaneous fat SF is present at the outer side of the muscle M and the visceral fat IF is present at the inner side of the muscle M.

A part of the subcutaneous fat SF immediately below which no muscle M is present moves downward by the action of gravity. When the visceral fat type and the subcutaneous fat type are compared, the downward movement of the subcutaneous fat SF is more notable in the subcutaneous fat type. Accordingly, as is understood from comparison of FIGS. 7 and 8, as a ratio of the subcutaneous fat area to an intraperitoneal fat area (hereinafter, referred to as a "subcutaneous fat rate") increases (as the fat type approaches from the visceral fat type to the subcutaneous fat type), the position of the maximum abdomen width Wmax in forward and backward directions of the subject 90 tends to be lower (closer to the reference plane $P_{REF}$).

That is, in the case of the subcutaneous fat type (FIG. 7), the determination line MW close to the position of the maximum abdomen width $W_{max}$ is sufficiently below the reference line $M_{REF}$ located at the uppermost position in the vertical direction. FIG. 7 illustrates a case in which the measurement line M[1] is selected as the determination line MW (TW=T[1]= LA[1]+LB[1]). Accordingly, the distance TW is a numerical value sufficiently less than the distance $T_{REF}$ (T[N]=LA[N]+ LB[N]) corresponding to the reference line $M_{REF}$. In other words, the shape index σ, which is the ratio (TW/$T_{REF}$) of the distance TW to the distance $T_{REF}$, is a numerical value sufficiently less than a maximum value of 1.

On the other hand, in the case of the visceral fat type (FIG. 8), the distance TW approximates or matches the distance $T_{REF}$ ($T_{REE}$=T[N]=LA[N]+LB [/V]) since the position of the maximum abdomen width $W_{max}$ is close to the reference line $M_{REF}$ (M[N]). Accordingly, the shape index σ is a numeral value close to the maximum value of 1. For example, when the measurement line M[N] is selected as the determination line MW (TW=T[N]=LA[N]+LB[N]) as in FIG. 8, the shape index σ is set at 1 (=TW/$T_{REF}$). As is understood from the above description, the shape index σ can function as an index for evaluating the cross-sectional shape of the abdomen 92 (i.e., index for classifying the fat type of the subject 90 into either the visceral fat type or the subcutaneous fat type) in terms of being a distance between the position of the maximum abdomen width $W_{max}$ and the reference plane $P_{REF}$ (a back surface of the subject 90).

Figure 9:
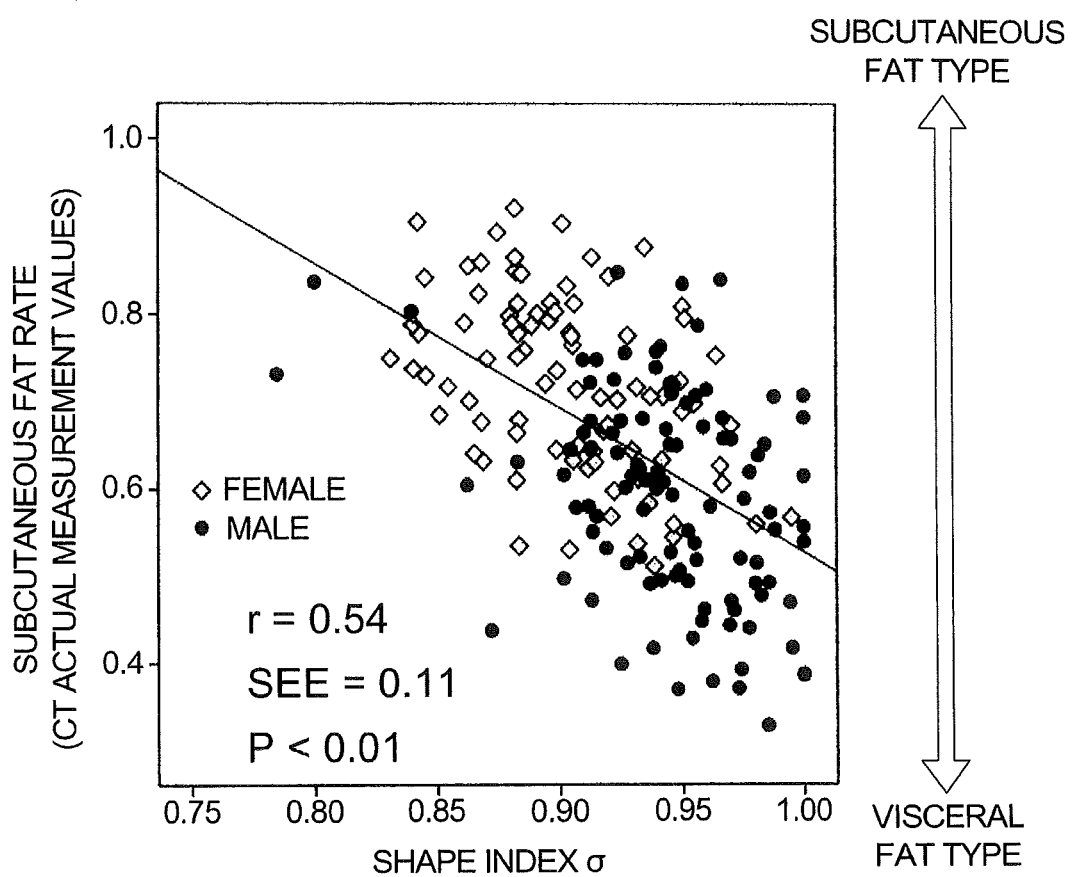
FIG. 9 is a correlation diagram of a shape index and a subcutaneous fat rate.

FIG. 9 is a correlation diagram showing a relationship between the shape index σ (horizontal axis) and the subcutaneous fat rate (vertical axis). Respective numerical values of the subcutaneous fat rate of FIG. 9 are actual measurement values measured by CT (Computed Tomography) scan. Respective numeric values of a correlation coefficient r of the shape index σ and the subcutaneous fat rate, a standard error of estimate SEE, and a risk rate p are also written in FIG. 9. The aforementioned tendency that the higher the subcutaneous fat rate (subcutaneous fat type), the closer to zero the numerical value of the shape index σ and the lower the subcutaneous fat rate (visceral fat type), the closer to 1 the numerical value of the shape index σ is also confirmed from FIG. 9. The above is the property of the shape index σ.

The arithmetic processor 66 in FIG. 5 calculates the visceral fat area based on the numerical values (ZH, ZL, R, Z) calculated by the biological impedance calculator 62, the abdomen width AW calculated by the abdomen width determiner 642, and the shape index σ calculated by the shape index calculator 644. As shown in FIG. 5, the arithmetic processor 66 includes an obesity evaluator 662 for evaluating whether an obesity degree (degree of obesity) of the subject 90 is high or low and an obesity index calculator 664 for calculating the visceral fat area of the subject 90.

The following equation (1) is used for calculation of the visceral fat area (unit: cm²).

$$A1 = a1 + b1 \times (AW^2 \times ZH)/ZL + c1 \times R/X \quad (1)$$

Numerical values of the respective coefficients (a1, b1, c1) of equation (1) are statistically (recursively) selected from an actual measurement result for a population with a specified number of samples. For example, if the subject 90 is a male (e.g., if a male is designated through an operation on the operating part 36), the respective coefficients of equation (1) may be set at the following numerical values:

$$a1=-24.36, b1=0.05950, c1=12.22.$$

If the subject 90 is a female, the respective coefficients of equation (1) may be set at the following numerical values:

$$a1=-17.41, b1=0.04031, c1=4.608.$$

Figure 10A:
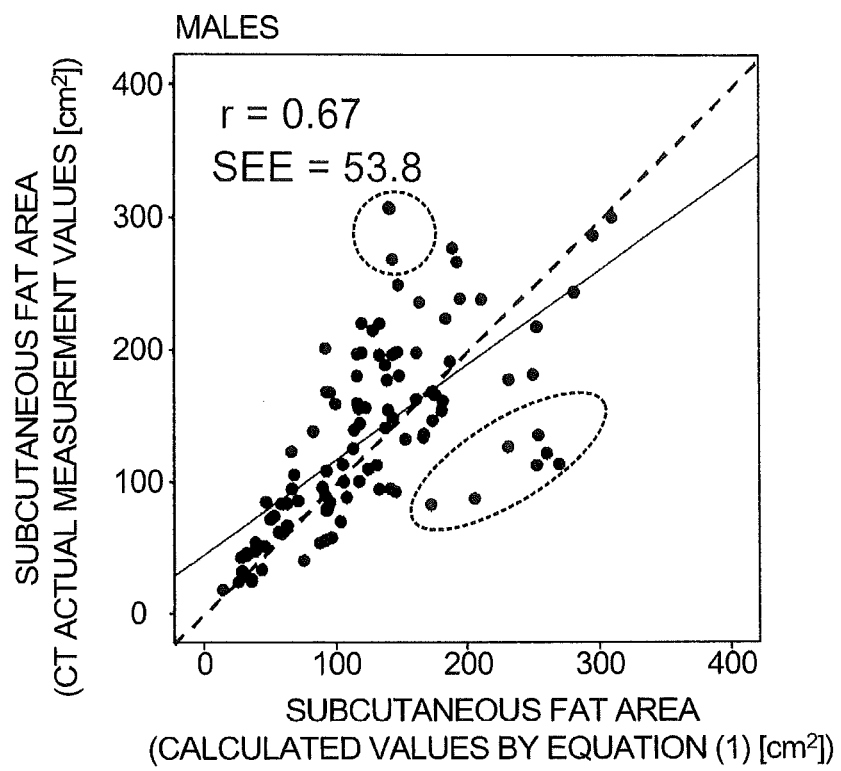
FIGS. 10A and 10B are correlation diagrams of calculated values (estimated values) and actual measurement values of a visceral fat area.
Figure 10B:
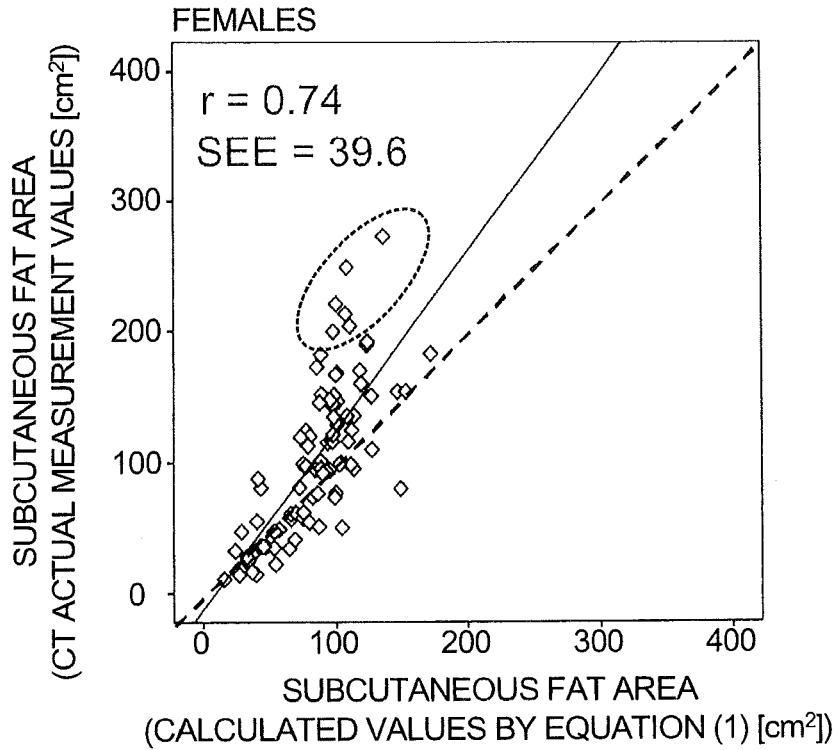

FIGS. 10A and 10B are correlation diagrams showing relationships between the visceral fat areas (calculated values) A1 calculated by equation (1) when the respective coefficients (a1, b1, c1) are set at the above values and actual measurement values of the visceral fat area using CT scan for males and females. As is understood from FIGS. 10A and 10B, when equation (1) is used, samples of which calculated values are divergent from the actual measurement values as shown by broken line in FIGS. 10A and 10B are present for both males and females. A result of a study by the present inventors confirmed a tendency that the samples (encircled by broken line) divergent from the actual measurement values had very high obesity degrees. According to the above knowledge, the arithmetic processor 66 of the first embodiment changes the equation used for calculation of the visceral fat area according to the obesity degree of the subject 90 as described in detail below.

Figure 11:
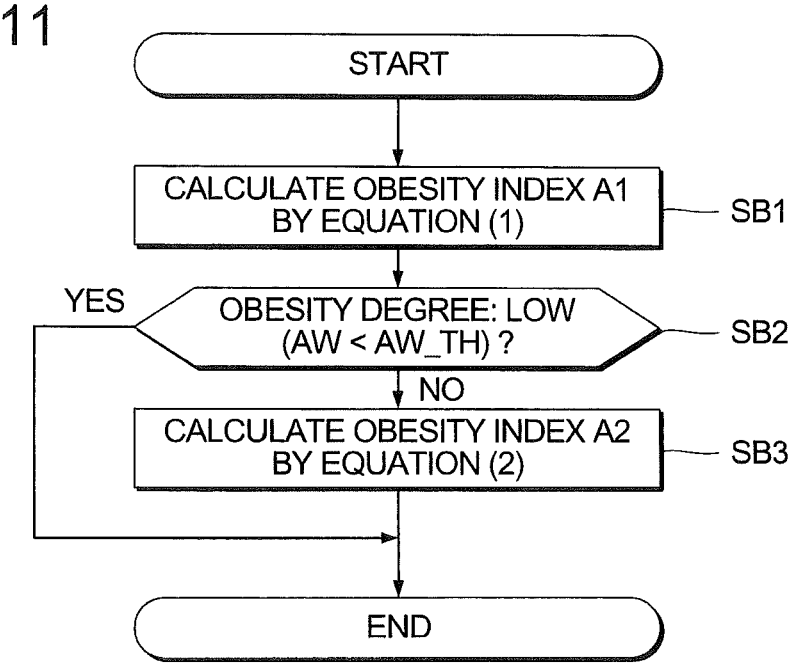
FIG. 11 is a flow chart showing the operation of an arithmetic processor.

FIG. 11 is a flow chart showing the operation of the arithmetic processor 66. A process of FIG. 11 is started after calculation by the biological impedance calculator 62 and the process of FIG. 6 by the distance measurement value calculator 64 are completed. When the process of FIG. 11 is started, the obesity index calculator 664 calculates the visceral fat area A1 using equation (1) and stores it in the storage 34 (SB1). Subsequently, the obesity evaluator 662 evaluates whether the obesity degree of the subject 90 is high or low (SB2).

Figure 12:
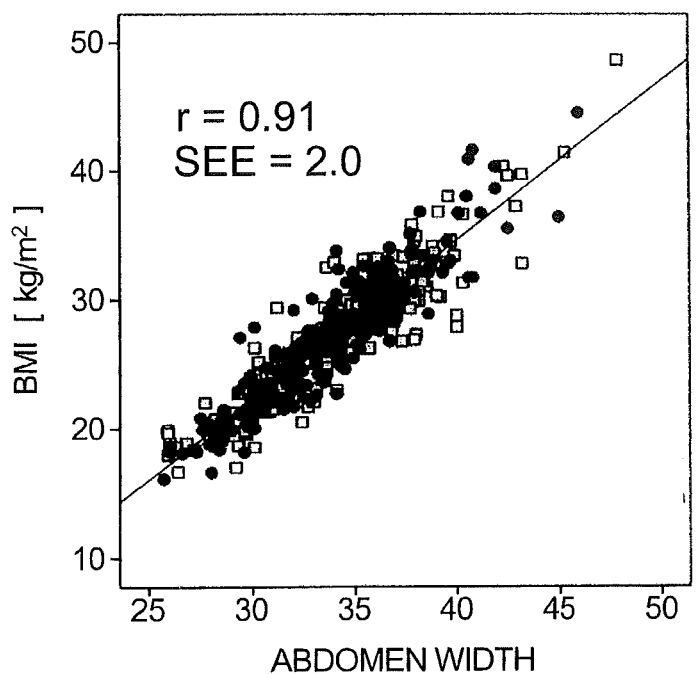
FIG. 12 is a correlation diagram of an abdomen width and a BMI.

FIG. 12 is a correlation diagram of a BMI (Body Mass Index) as an index for obesity degree and the abdomen width (actual measurement value) of the subject 90. As is understood from FIG. 12, the abdomen width and the BMI are highly correlated (r=0.91). In consideration of the above tendency, the obesity evaluator 662 of the first embodiment evaluates whether the obesity degree of the subject 90 is high or low using the abdomen width AW determined by the abdomen width determiner 642 as the index for the obesity degree of the subject 90. Specifically, after comparing the abdomen width AW calculated by the abdomen width determiner 642 with a predetermined threshold value AW_TH, the obesity evaluator 662 evaluates that the obesity degree of the subject 90 is high if the abdomen width AW exceeds the threshold value AW_TH while evaluating that the obesity degree of the subject 90 is low if the abdomen width AW is below the threshold value AW_TH. The threshold value AW_TH is set at a numerical value of, e.g., about 30 cm to 35 cm.

If the obesity evaluator 662 evaluates that the obesity degree is low (AW_<AW_TH) (SB2: YES), the arithmetic processor 66 ends the process of FIG. 11. That is, the result (A1) of calculation using equation (1) in step SB1 is determined as the visceral fat area. On the other hand, if the obesity evaluator 662 evaluates that the obesity degree is high (AW>AW_TH) (SB2: NO), the obesity index calculator 664 calculates a visceral fat area A2 (unit: cm$^2$) using equation (2) different from equation (1) and stores it in the storage 34 (SB3). Equation (2) is a function with the visceral fat area A1 calculated by equation (1) and the shape index σ calculated by the shape index calculator 644 as variables.

$$A2 = a2 + b2 \times A1 + c2 \times \sigma \qquad (2).$$

Numerical values of the respective coefficients (a2, b2, c2) of equation (2) are statistically (recursively) selected from an actual measurement result for a population with a specified number of samples. For example, if the subject 90 is a male (e.g., if a male is designated through an operation on the operating part 36), the respective coefficients of equation (2) may be set at the following numerical values:

$$a2=-414.4, b2=0.4659, c2=1062.$$

Furthermore, if the subject 90 is a female, the respective coefficients of equation (2) may be set at the following numerical values:

$$a2=-136.1, b2=0.6173, c2=677.0.$$

As is understood from equation (2), the greater the numerical value of the shape index σ, the greater the numerical value of the visceral fat area A2. As described above with reference to FIG. 9, the lower the subcutaneous fat rate (visceral fat type), the greater the numerical value of the shape index σ. Thus, the lower the subcutaneous fat rate, the greater the numerical value of the visceral fat area A2 of equation (2). That is, the third term (c2×σ) including the shape index σ in equation (2) functions as a correction term which corrects the visceral fat area A1 calculated by equation (1) according to the obesity type (visceral fat type versus subcutaneous fat type) of the subject 90. The numerical values of the visceral fat areas (A1, A2) calculated in the process of FIG. 11 are shown on the display 38.

Figure 13A:
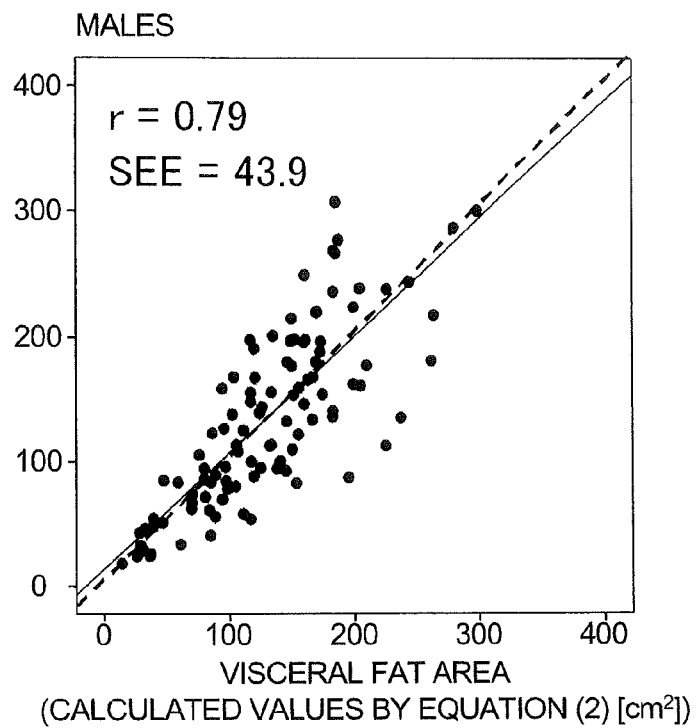
FIGS. 13A and 13B are correlation diagrams of calculated values and actual measurement values of the visceral fat area.
Figure 13B:
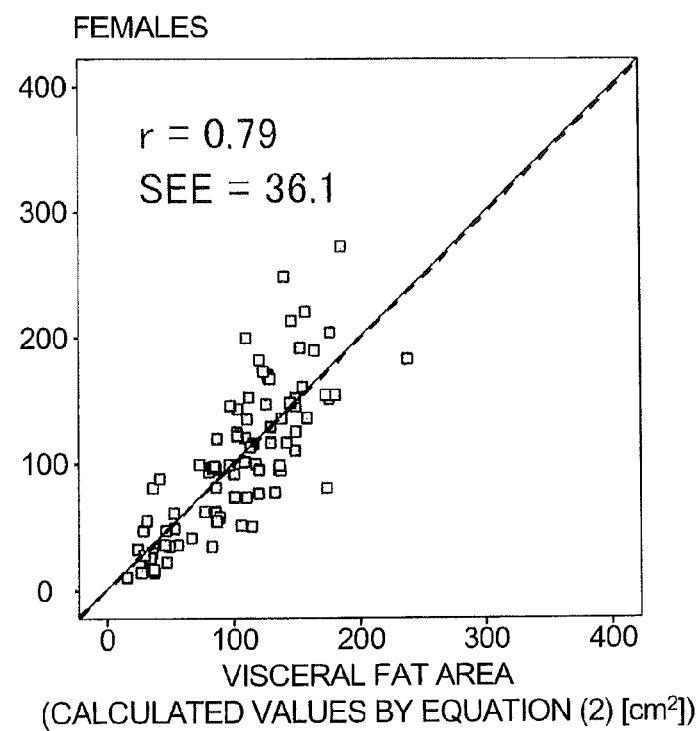

FIGS. 13A and 13B are correlation diagrams showing a relationship between the visceral fat areas (calculated values) A2 calculated by equation (2) when the respective coefficients (a2, b2, c2) are set at the respective numerical values described above and actual measurement values of the visceral fat area using CT scan for each sex for the same populations as in FIGS. 10A and 10B. A correlation coefficient r and a standard error of estimate SEE of FIGS. 13A and 13B are improved as compared with the case of FIGS. 10A and 10B using equation (1). In other words, it is understood that, by using equation (2) for the subject 90 with a high obesity degree, a divergence between the calculated value and the actual measurement value can be reduced as compared with the case of FIG. 10 using equation (1).

Figure 14A:
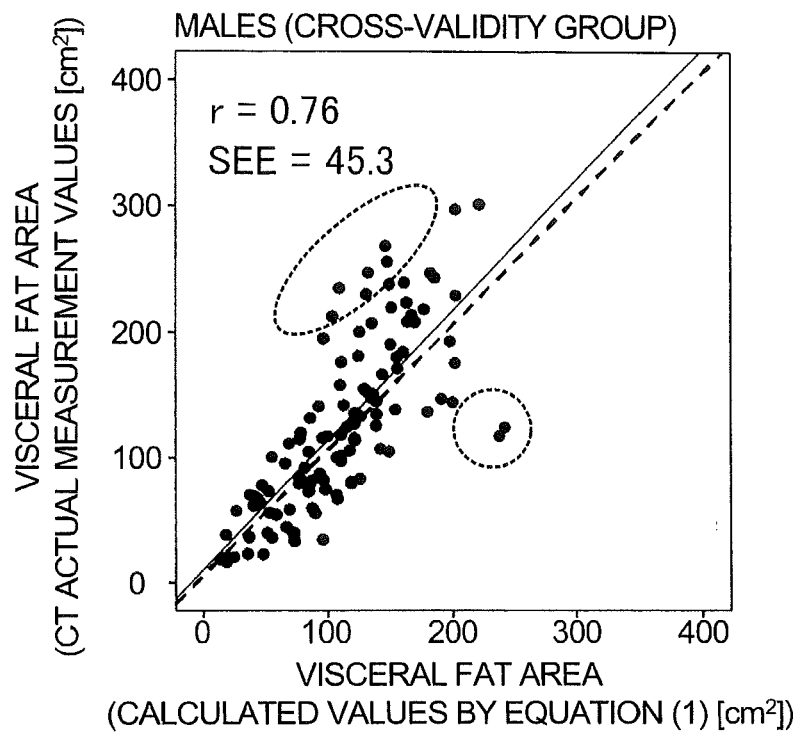
FIGS. 14A and 14B are correlation diagrams of calculated values and actual measurement values of the visceral fat area of a cross-validity group (males), FIG. 15 are correlation diagrams of calculated values and actual measurement values of the visceral fat area of a cross-validity group (females)
Figure 14B:
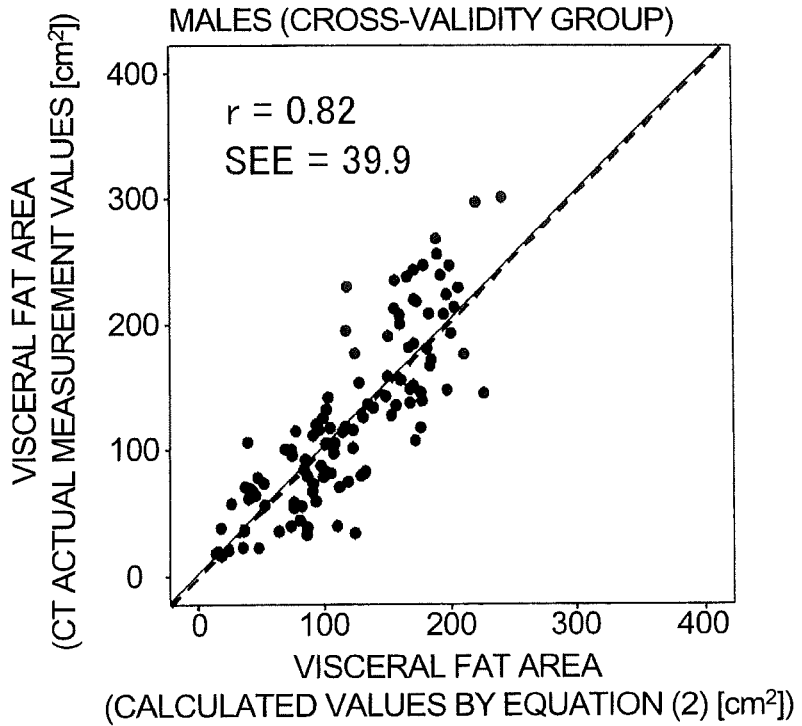
Figure 15A:
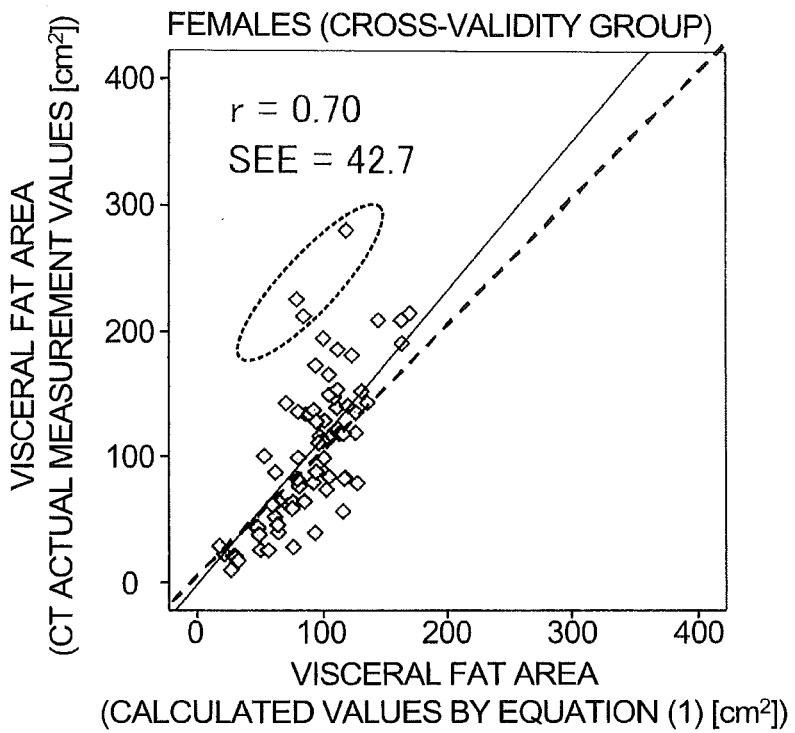
Figure 15B:
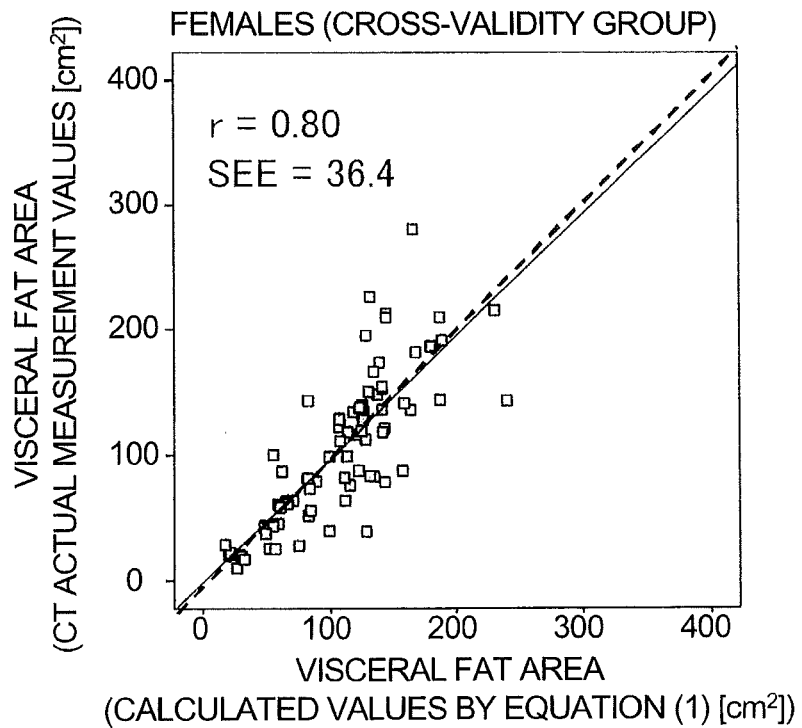

FIGS. 14A, 14B, 15A, and 15B are correlation diagrams showing a relationship between the visceral fat areas (calculated values) calculated by equations (1) and (2) and actual measurement values using CT scan for populations (cross-validity groups) different from those of FIGS. 10 and 13. The cross-validity groups are composed of samples (obese people) under conditions (age, BMI, abdominal circumference) shown in FIG. 16. FIGS. 14A and 14B show visceral fat areas of males, and FIGS. 15A and 15B show visceral fat areas of females. FIGS. 14A and 15A show a case in which equation (1) is employed, and FIGS. 14B and 15B show a case in which equation (2) is employed.

It is confirmed for both male and female cross-validity groups that divergences between the calculated values and the actual measurement values are reduced (accuracy in estimating the visceral fat area is improved) as compared with the case in which equation (1) is employed by employing equation (2) for calculation of the visceral fat areas of obese people. Accordingly, the above equation (2) can be evaluated as a sufficiently reasonable equation for estimating the visceral fat area of an obese person.

As described above, in the first embodiment, the visceral fat area can be estimated with high accuracy even when the obesity degree of the subject 90 is high as compared with a construction using only equation (1) since the equation for calculating the visceral fat area is changed according to the obesity degree of the subject 90 (equation (2) is used for calculation of the visceral fat area of the subject 90 with a high obesity degree). Furthermore, since equation (2) includes the shape index σ as the variable and a difference in the cross-sectional shape of the abdomen 92 resulting from the obesity type (visceral fat type versus subcutaneous fat type) of the subject 90 is reflected on the shape index σ, there is an advantage of being able to calculate the visceral fat area with high accuracy regardless of whether the obesity type is the visceral fat type or the subcutaneous fat type.

In the first embodiment, the distance TW calculated from the distance measurement signals is commonly used for calculation of the abdomen width AW by the abdomen width determiner 642 (Step SA5) and calculation of the shape index σ by the shape index calculator 644 (Step SA6). Thus, there is an advantage of reducing a processing amount by the controller 32 as compared with a construction in which the abdomen width AW and the shape index σ are independently calculated.

In the first embodiment, the abdomen width AW determined by the abdomen width determiner 642 is used for evaluation of the obesity degree by the obesity evaluator 662. As a result, there is an advantage of reducing a processing amount necessary for evaluation of the obesity degree as compared with a construction in which an independent index indicating the obesity degree is calculated and used for evaluation in step SB2 (construction in which the abdomen width AW is not used for evaluation of the obesity degree).

In the first embodiment, the visceral fat area A1 calculated by equation (1) is used for calculation of equation (2) by the obesity index calculator 664. As a result, there is an advantage of reducing a processing amount necessary for calculation of the visceral fat area A2 as compared with a construction in which the visceral fat area A2 is calculated independently of the visceral fat area A1 (that is, a construction in which the visceral fat area A1 is not used for calculation of the visceral fat area A2).

Second Embodiment

A second embodiment of the present invention will be described below.

In the second embodiment, an abdominal circumference (waist) of a subject 90 is calculated as an obesity index. Note that elements whose actions and functions are equivalent to those of the first embodiment in respective modes illustrated below are identified by the same reference numerals as in the above description, and detailed description thereof is appropriately omitted.

Figures 16, 17:
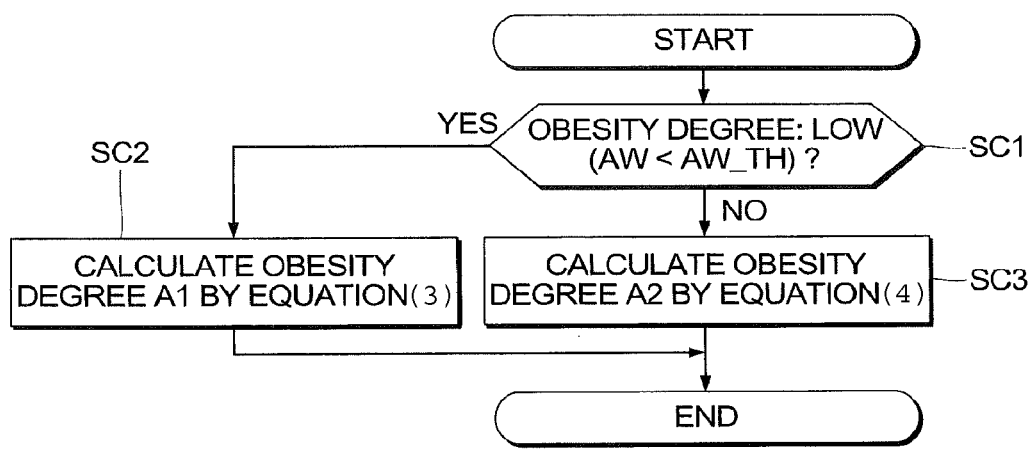
FIG. 16 is a table showing conditions of the cross-validity groups of FIGS. 14 and 15.
FIG. 17 is a flow chart showing the operation of an arithmetic processor according to a second embodiment.

An arithmetic processor 66 (obesity evaluator 662, obesity index calculator 664) of the second embodiment performs a process illustrated in FIG. 17 instead of the process illustrated in FIG. 11. When the process illustrated in FIG. 17 starts, the obesity evaluator 662 evaluates whether an obesity degree of the subject 90 is high or low (SC1). For evaluation of the obesity degree, an abdomen width AW is used similarly to the first embodiment.

If the obesity evaluator 662 evaluates that the obesity degree is low (e.g., AW<AW_TH) (SC1: YES), the obesity index calculator 664 calculates an abdominal circumference C1 (unit: cm) corresponding to the abdomen width AW using equation (3) illustrated below and stores it in the storage 34 (SC2).

$$C1 = a3 \times AW + b3 \quad (3)$$

Numerical values of the respective coefficients (a3, b3) of equation (3) are statistically (recursively) selected from an actual measurement result for a population with a specified number of samples. For example, the respective coefficients of equation (3) may be set at the following numerical values (common for both males and females):

$$a3=2.728, b3=-10.03.$$

On the other hand, if the obesity evaluator 662 evaluates that the obesity degree is high (e.g., AW>AW_TH) (SC1: NO), the obesity index calculator 664 calculates an abdominal circumference C2 (unit: cm) corresponding to the abdomen width AW and the shape index σ using equation (4) illustrated below and stores it in the storage 34 (SC3). In other words, in the second embodiment, the abdominal circumference C1 is calculated by equation (3) not including the shape index σ when the obesity degree of the subject 90 is low and the abdominal circumference C2 is calculated by equation (4) including the shape index σ when the obesity degree of the subject 90 is high.

$$C2 = a4 \times AW + b4 + c4 \times \sigma \quad (4)$$

Numerical values of the respective coefficients (a4, b4, c4) of equation (4) are statistically (recursively) selected from an actual measurement result for a specified population. For example, the respective coefficients of equation (4) may be set at the following numerical values (common for both males and females):

$$a4=3.544, b4=-39.62, c4=92.08.$$

As is understood from FIGS. 7 and 8, the abdomen 92 of the subcutaneous fat type (FIG. 7) has a tendency that the abdominal circumference is relatively smaller than the maximum abdomen width $W_{max}$ and the abdomen 92 of the visceral fat type (FIG. 8) has a tendency that the abdominal circumference is relatively greater than the maximum abdomen width $W_{max}$. On the other hand, as is understood from the content of equation (4), the greater the numerical value of the shape index σ (visceral fat type), the greater the numerical value of the abdominal circumference C2, and the less the numerical value of the shape index σ (subcutaneous fat type), the less the numerical value of the abdominal circumference C2. That is, the abdominal circumference C2 calculated by equation (4) is consistent with the above correlation tendency of the fat type and the abdominal circumference.

Figure 18A:
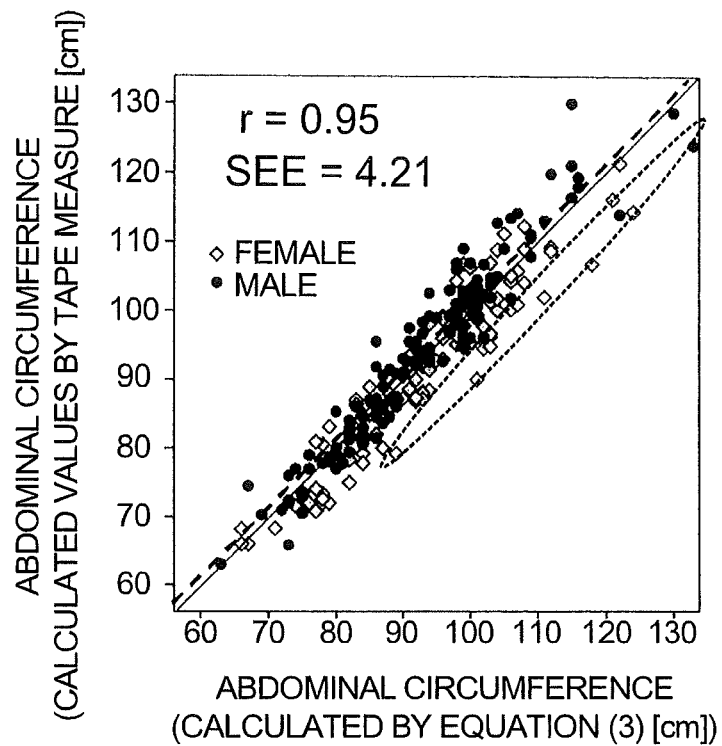
FIGS. 18A and 18B are correlation diagrams of calculated values and actual measurement values of an abdominal circumference.
Figure 18B:
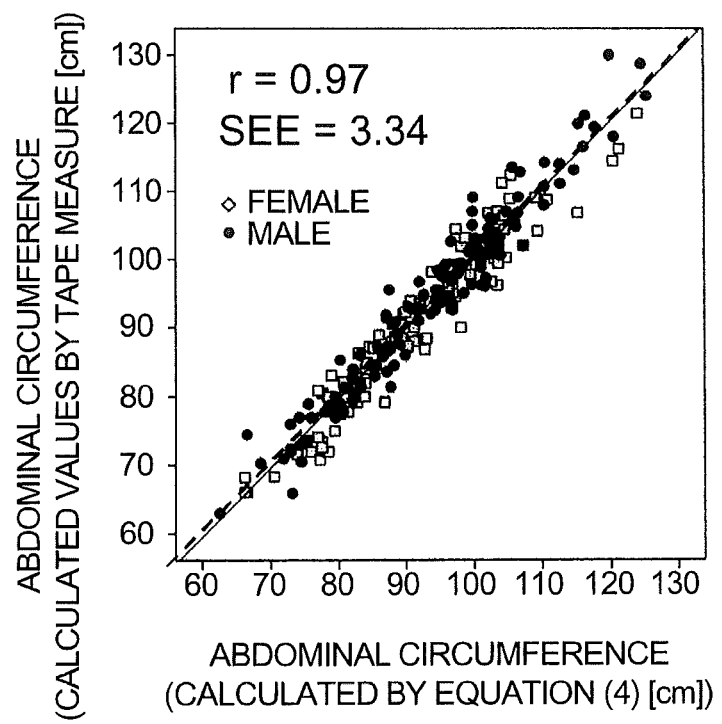

FIG. 18A is a correlation diagram of the abdominal circumferences (calculated values) C1 calculated by equation (3) the respective coefficients of which are set at the above respective numerical values and actual measurement values of the abdominal circumference measured by a tape measure. A tendency that the calculated value of equation (3) and an actual measurement value are likely to diverge for samples with high obesity degrees (encircled by broken line) is understood from FIG. 18A. On the other hand, FIG. 18B is a correlation diagram of the abdominal circumferences (calculated values) C2 calculated by equation (4) the respective coefficients of which are set at the above respective numerical values and actual measurement values by a tape measure. A correlation coefficient r and a standard error of estimate SEE of FIG. 18B are improved as compared with the case of FIG. 18A using equation (3). In other words, it can be understood that, by using equation (4) for the subject 90 with a high obesity degree, a divergence between the calculated value and the actual measurement value can be reduced as compared with the case of FIG. 18A using equation (3).

Figure 19A:
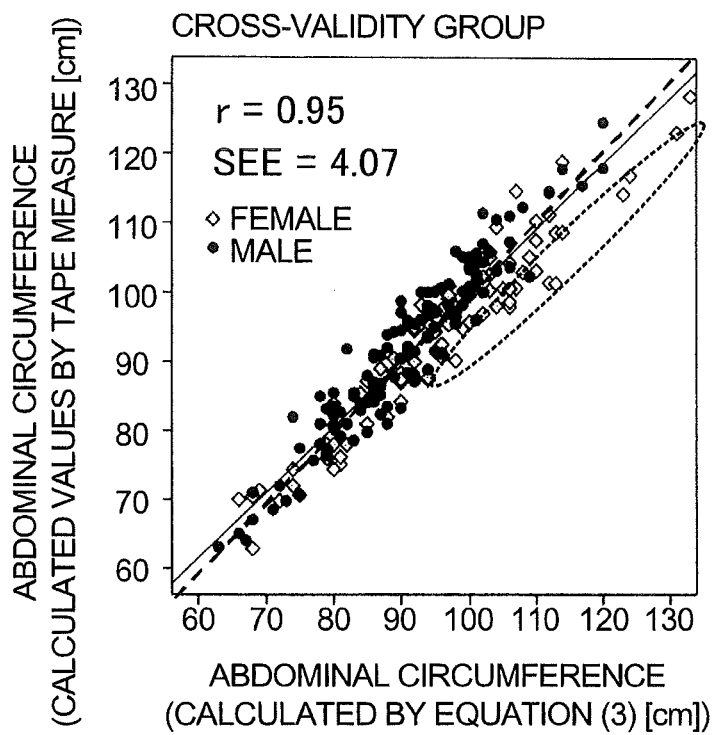
FIGS. 19A to 19C are correlation diagrams of calculated values and actual measurement values of abdominal circumferences of cross-validity groups.
Figure 19B:
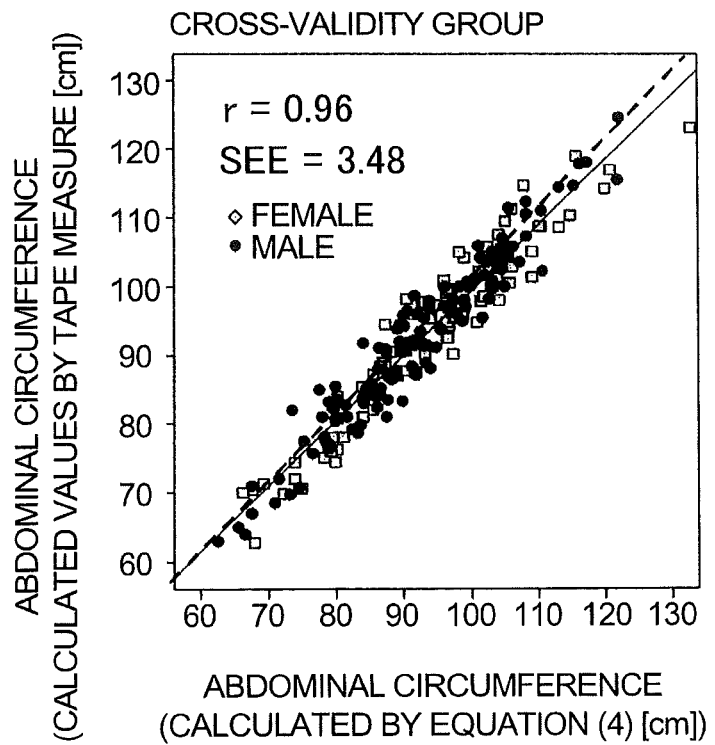
Figures 19C, 20:
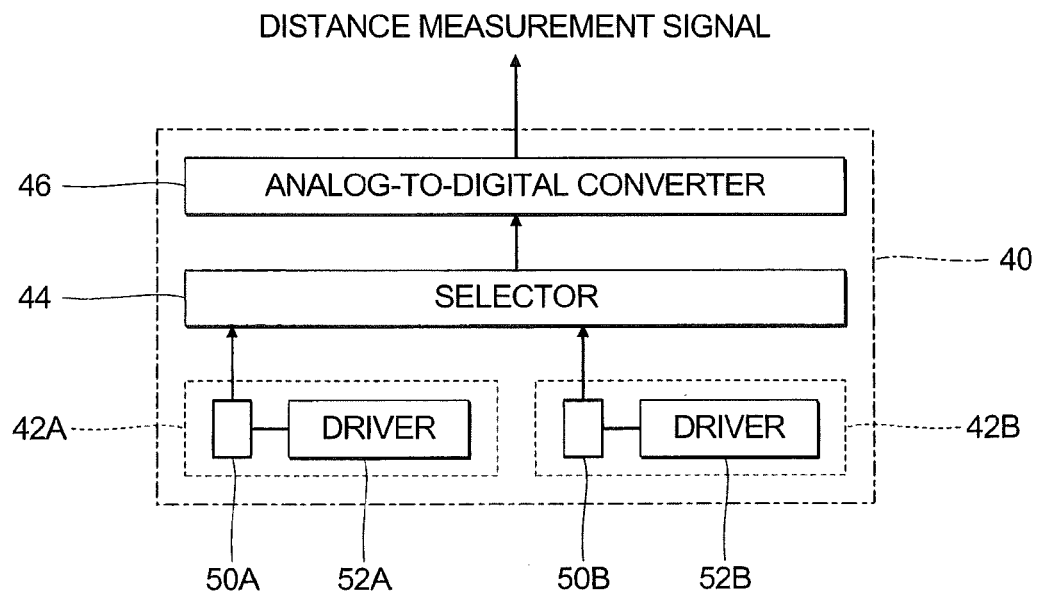
FIG. 20 is a block diagram of a measuring portion according to a modification.

FIGS. 19A and 19B are correlation diagrams of abdominal circumferences (calculated values) calculated by equation (3) or (4) and actual measurement values of the abdominal circumference measured by a tape measure for populations (cross-validity groups) different from FIG. 18. The cross-validity group is made up of samples (obese people) under conditions shown in FIG. 19C. Comparison of FIGS. 19A and 19B exemplifies that, by employing equation (4) for calculation of the abdominal circumference of an obese person, a divergence between the calculated value and the actual measurement value is reduced also for the cross-validity group as compared with the case in which equation (3) is employed (FIG. 19A). Thus, the above equation (4) can be evaluated as a sufficiently reasonable equation for estimating the abdominal circumference of an obese person.

In second embodiment, effects similar to those of the first embodiment are also realized. Specifically, since the equation for calculating the abdominal circumference is changed depending on whether the obesity degree of the subject 90 is high or low in the second embodiment, it is possible to estimate the abdominal circumference with high accuracy even if the obesity degree of the subject 90 is high as compared with a construction using only equation (3). Since equation (4) includes the shape index σ, there is an advantage of being able to calculate the abdominal circumference with high accuracy regardless of whether the obesity type is the visceral fat type or the subcutaneous fat type.

Other Variations and Modifications

The above respective embodiments can be modified in various manners. Modes of specific modifications are illustrated below. Two or more modes freely selected from the following examples can be appropriately combined.

(1) First Modification

Although each of the distance meters 42A and 42B includes N (a plurality of) distance measuring sensors 50 in the above respective embodiments, each of the distance meters 42A and 42B may include one distance measuring sensor 50. For example, in a measuring portion 40 of FIG. 20, a distance meter 42A includes one distance measuring sensor 50A and a driver 52A and a distance meter 42B includes one distance measuring sensor 50B and a driver 52B. The driver 52A moves the distance meter 50A in the vertical direction so that a reference point p0 of the distance measuring sensor 50A is located on the respective reference lines M[1] to M[N]. Similarly, the driver 52B moves the distance measuring sensor 50B to the respective positions of the reference lines M[1] to M[N]. As a result, the distance measuring sensor 50A outputs distance measurement signals corresponding to the respective distances LA[1] to LA[N] and the distance measuring sensor 50B outputs distance measurement signals corresponding to the respective distances LB[1] to LB[N]. A selector 44 selects and outputs the distance measurement signals generated by the respective distance measuring sensors 50A, 50B.

(2) Second Modification

Although the ratio ($TW/T_{REF}$) of the distance TW to the distance $T_{REF}$ is calculated as the shape index σ in the above respective embodiments, the calculation method for the shape index σ is not limited to the above illustrated one. For example, the shape index c may be calculated based on a difference between the distance TW and the distance $T_{REF}$. Specifically, if the shape index σ is so defined that the greater the difference |TW−$T_{REF}$| between the distance TW and the distance $T_{REF}$, the smaller the numerical value of the shape index σ (e.g., σ=c−|TW−$T_{REF}$| where c is a predetermined value), it can be applied for calculation of the obesity index similarly to the shape index σ (σ=TW/$T_{REF}$) of the first embodiment.

Although the shape index σ is so calculated in the above respective examples that the smaller the numerical value of the distance TW relative to the distance $T_{REF}$, the smaller the numerical value of the shape index σ, a relationship between the magnitude relationship of the distances TW and $T_{REF}$ and the increase and decrease of the shape index σ can be reversed. For example, if a ratio ($T_{REF}$/TW) of the distance $T_{REF}$ to the distance TW or a difference |TW−$T_{REF}$| between the distances TW and $T_{REF}$ is the shape index σ, the shape index σ may be set at a greater numerical value as the numerical value of the distance TW becomes relatively shorter than the distance $T_{REF}$ (subcutaneous fat type). In the above construction, contrary to the first embodiment, the contents and coefficients of equations (2) and (4) are so changed that the greater the shape index σ (subcutaneous fat type), the smaller the numerical value of the visceral fat area A2 or the abdominal circumference C2.

As is understood from the above example, a variable corresponding to a discrepancy (ratio or difference) of the distance TW (LA[n]+LB[n]) corresponding to the determination line MW and the distance $T_{REF}$ (LA[N]+LB[/V]) corresponding to the reference line $M_{REF}$ may be suitably used as the shape index σ. Specifically, the shape index σ is so selected that the more distant from the reference plane $P_{REF}$ (back surface of the subject 90) in forward and backward directions of the subject 90 the position of the maximum abdomen width $W_{max}$ (position of the determination line MW) (i.e., the lower the subcutaneous fat rate), the greater the numerical values of the visceral fat area A2 and the abdominal circumference C2.

The calculation of the shape index σ according to the discrepancy between the distance TW and the distance $T_{REF}$ is not essential to the present invention. For example, considering the tendency that the determination line MW becomes closer to the reference plane $P_{REF}$ as the subcutaneous fat rate increases (subcutaneous fat type) as is understood from FIGS. 7 and 8, it is also possible to employ a construction for calculating the shape index σ according to a distance δ between the reference plane $P_{REF}$ and the determination line MW. Specifically, a ratio of the distance δ to a predetermined value $δ_{max}$ is calculated as the shape index σ (σ=δ/$δ_{max}$). The predetermined value $δ_{max}$ is a distance between the $N^{th}$ measurement line M[N] and the reference plane $P_{REF}$ (i.e., a maximum value of the distance δ) as shown in FIGS. 7 and 8. In the above example, similar to the shape index σ of the first embodiment, the higher the subcutaneous fat rate of the subject 90 (subcutaneous fat type), the smaller the numerical value of the distance δ relative to the predetermined value $δ_{max}$. As a result, the shape index σ becomes a numerical value close to zero (meanwhile the shape index σ has a numerical value close to 1 in the case of the visceral fat type).

As is understood from the above example, the shape index σ is a variable corresponding to the cross-sectional shape of the abdomen 92 of the subject 90. As illustrated above, the position of the maximum abdomen width $W_{max}$ (distance from the reference plane $P_{REF}$) in forward and backward directions of the subject 90 can be exemplified as the cross-sectional shape of the abdomen 92 that can be reflected on the shape index σ.

(3) Third Modification

The abdomen width determiner 642 determines the abdomen width AW in any manner. For example, in an example in which the abdomen width AW measured by a measuring tool such as a ruler or a tape measure is input through an operation on the operating part 36, the abdomen width determiner 642 determines (acquires) the abdomen width AW in accordance with the operation on the operating part 36. In addition to the above example, any known technology can be employed to determine the abdomen width AW.

(4) Fourth Modification

Although the abdomen width AW is used to evaluate the obesity degree of the subject 90 in the above respective embodiments, the obesity degree may be evaluated in any manner. For example, since biological information such as BMI, weight and biological impedance is correlated to the obesity degree, an example in which the obesity evaluator 662 evaluates whether the obesity degree of the subject 90 is high or low based on these pieces of biological information is also suitably employed. The biological information as a basis of the obesity degree is input from the outside, for example, through an operation on the operating part 36. Furthermore, an example in which a mechanism for measuring biological information such as BMI and weight is installed in the measuring apparatus 100 is also preferable.

(5) Fifth Modification

The obesity index is not limited to the visceral fat area exemplified in the first embodiment and the abdominal circumference exemplified in the second embodiment. For example, a visceral fat level, a visceral fat rate or a subcutaneous fat rate can be calculated as an obesity index. The visceral fat level may be calculated by dividing the visceral fat area calculated by the method of the first embodiment by a predetermined value (e.g., 10). The visceral fat rate may be calculated as a ratio of the visceral fat area to the intraperitoneal fat area. The subcutaneous fat rate is calculated by subtracting the visceral fat rate from a predetermined value (100%). Furthermore, as is understood from equation (2) and equation (4), an equation obtained by adding a correction term including the shape index σ to a known equation for calculating the obesity index is preferably used to calculate the obesity index of the subject 90 with a high obesity degree.

(6) Sixth Modification

Although the distance meters 42A and 42B are arranged to face each other at the opposite sides of the abdomen 92 of the subject 90 in the above embodiments, it is also possible to omit one of the distance meters 42A and 42B, considering that the transverse section of the abdomen 92 is substantially line-symmetric. For example, in an example without distance meter 42B, twice the minimum value of the distances LA[1] to LA[N] may be set as the distance TW and twice the distance LA[N] may be set as the distance $T_{REF}$.

What is claimed is:

1. A measuring apparatus comprising:
   an abdomen width determining unit for determining an abdomen width of a subject;
   an obesity evaluating unit for evaluating an obesity degree of the subject; and
   an obesity index calculating unit for calculating an obesity index of the subject corresponding to the abdomen width of the subject using a first equation when the obesity evaluating unit has evaluated that the obesity degree of the subject is low and calculating an obesity index of the subject corresponding to the abdomen width of the subject using a second equation different from the first equation when the obesity evaluating unit has evaluated that the obesity degree of the subject is high.

2. The measuring apparatus according to claim 1, further comprising a shape index calculating unit for calculating a shape index corresponding to a cross-sectional shape of an abdomen of the subject, wherein the second equation includes the shape index as a variable.

3. The measuring apparatus according to claim 2, further comprising a measuring portion for generating a distance measurement signal corresponding to a distance to a measurement point on a measurement line on an abdomen surface of the subject for each of a plurality of measurement lines which are parallel to a lateral direction of the subject, which are located at different positions in forward and backward directions, and each of which has a section passing through the abdomen, wherein the shape index calculating unit calculates the shape index corresponding to a discrepancy between a first distance indicated by a distance measurement signal corresponding to a determination line with a longest section passing through the abdomen out of the plurality of the measurement lines and a second distance indicated by a distance measurement signal corresponding to a reference line selected from the plurality of the measurement lines.

4. The measuring apparatus according to claim 3, wherein:

the measuring portion includes a first distance meter and a second distance meter which face each other across the abdomen of the subject and each of which generates the distance measurement signals corresponding to the respective measurement lines; and the shape index calculating unit calculates the shape index corresponding to a discrepancy between a sum of the first distances indicated by the distance measurement signals generated for the determination line by the respective first and second distance meters and a sum of second distances indicated by the distance measurement signals generated for the reference line by the respective first and second distance meters.

5. The measuring apparatus according to claim 4, wherein the abdomen width determining unit determines a numerical value obtained by subtracting the first distances indicated by the distance measurement signals generated for the determination line by the respective first and second distance meters from a distance between the first and second distance meters as the abdomen width.

6. The measuring apparatus according to claim 2, wherein:

the obesity index is a visceral fat area of the subject; and the shape index calculating unit calculates the shape index so that the more distant from the back surface of the subject in forward and backward directions of the subject at a position where the abdomen width is greatest, the greater the visceral fat area calculated by the obesity index calculating unit.

7. The measuring apparatus according to claim 6, wherein the obesity index calculating unit calculates the visceral fat area corresponding to the abdomen width using the first equation, evaluates the visceral fat area to be the calculated value if the obesity evaluating unit evaluates that the obesity degree is low, and calculates the visceral fat area using the second equation including the visceral fat area calculated by the first equation as the variable if the obesity evaluating unit evaluates that the obesity degree is high.

8. The measuring apparatus according to claim 2, wherein:

the obesity index is an abdominal circumference of the subject; and the shape index calculating unit calculates the shape index so that the more distant from the back surface of the subject in the forward and backward directions of the subject at a position where the abdomen width is greatest, the greater the numerical value of the abdominal circumference calculated by the obesity index calculating unit.

9. The measuring apparatus according to claim 1, wherein the obesity evaluating unit evaluates whether the obesity degree of the subject is high or low based on the abdomen width determined by the abdomen width determining unit.

* * * * *